United States Patent [19] Nakamura et al.

[11] 4,031,134

[45] June 21, 1977

[54] PHENOXY CARBOXYLIC ACID DERIVATIVE

[75] Inventors: Yasushi Nakamura, Ibaragi; Kunio Agatsuma; Yoshihiro Tanaka, both of Takarazuka; Shunji Aono, Toyonaka, all of Japan

[73] Assignee: Sumitomo Chemical Company, Limited, Osaka, Japan

[22] Filed: Sept. 25, 1972

[21] Appl. No.: 292,110

Related U.S. Application Data

[62] Division of Ser. No. 26,412, April 7, 1970, Pat. No. 3,716,583.

[30] Foreign Application Priority Data

| | | |
|---|---|---|
| Apr. 16, 1969 | Japan | 44-029905 |
| Apr. 16, 1969 | Japan | 44-029907 |
| May 2, 1969 | Japan | 44-034166 |
| May 2, 1969 | Japan | 44-034167 |
| Oct. 3, 1969 | Japan | 44-080041 |
| Oct. 3, 1969 | Japan | 44-080042 |
| Dec. 19, 1969 | Japan | 44-102809 |
| Dec. 23, 1969 | Japan | 44-104194 |

[52] U.S. Cl. .......... 260/520 C; 260/473 G

[51] Int. Cl.$^2$ .......... C07C 65/14; C07C 69/76

[58] Field of Search .......... 260/520, 473 G

[56] References Cited

UNITED STATES PATENTS

| | | | |
|---|---|---|---|
| 2,370,256 | 2/1945 | Niederl | 260/520 |
| 2,444,594 | 7/1948 | Day et al. | 260/520 |
| 2,482,706 | 9/1949 | Day | 260/473 G |
| 2,541,003 | 2/1951 | Day et al. | 260/473 G |
| 3,097,139 | 7/1963 | Thorp | 260/521 R |
| 3,169,144 | 2/1965 | Cavallini et al. | 260/520 |
| 3,262,850 | 7/1966 | Jones et al. | 260/473 G |
| 3,470,235 | 9/1969 | Jackson et al. | 260/473 G |
| 3,630,715 | 12/1971 | Guttag | 260/473 G |

FOREIGN PATENTS OR APPLICATIONS

| | | |
|---|---|---|
| 2,017,331 | 11/1970 | Germany |
| 916,242 | 1/1963 | United Kingdom |

OTHER PUBLICATIONS

Bourley "Medicinal Chemistry" 3rd Ed. (1970) pp. 25–28.

*Primary Examiner*—Robert Gerstl

*Attorney, Agent, or Firm*—Stevens, Davis, Miller & Mosher

[57] ABSTRACT

Novel anti-atherosolerosis agents having the formula,

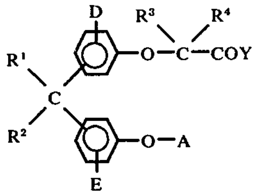

wherein typical examples of $R^1$ and $R^2$ are hydrogen, $C_1$-$C_8$ alkyl, phenyl, benzyl and phenethyl, or $R^1$ and $R^2$ may form cycloalkylidene together with a carbon atom bonded therewith; $R^3$ and $R^4$ each is hydrogen or $C_1$-$C_4$ alkyl; Y is hydroxyl, $C_1$-$C_4$ alkoxy, phenoxy or an amine residue; A is hydrogen or a group of the formula,

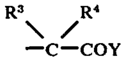

wherein $R^3$, and $R^4$ and Y have the same meanings as defined above; and D and E each is hydrogen or halogen.

These compounds are produced, for example, by reacting a bisphenolic compound of the formula,

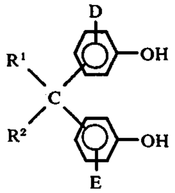

with chloroform and a ketone compound of the formula, $$R^3 - CO - R^4$$

in the presence of an alkali. Alternatively, they are produced by reacting the bisphenolic compound with α-halogeno- or α-hydroxycarboxylic acid derivative of the formula,

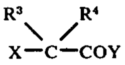

wherein $R^1$, $R^2$, $R^3$, $R^4$, D, E and Y have the same meanings as defined above; and X is halogen or hydroxyl.

3 Claims, No Drawings

PHENOXY CARBOXYLIC ACID DERIVATIVE

This is a division of application Ser. No. 26,412, filed Apr. 7, 1970, now U.S. Pat. No. 3,716,583.

This invention relates to novel anti-atherosclerosis agents. More particularly, the invention pertains to novel agents which are useful for the lowering of elevated levels of cholesterol or lipids.

Atherosclerosis is an adult disease for which there is no known satisfactory cure. Although the cause for atherosclerosis is not yet known in spite of discussions in the academic circles, it has broadly been recognized that one of the most significant histo-pathological manifestations of atherosclerosis is the deposition of lipids in the blood. Accordingly, research has been directed to the disturbed metabolism of lipids, and attention has been given to the extraordinarily elevated level of cholesterol in the blood.

A number of experimental and clinical facts have been reported, which indicate the relationship between atherosclerosis and elevated blood cholesterol or lipid level. Hence, the development of agents to reduce the elevated blood cholesterol or lipid level is considered extremely important for the prevention of atheroclerosis.

Concentrated efforts have heretofore been made for the development of such agents for lowering cholesterol or lipids and a number of compounds have been tested clinically, but none of them have been proved to be completely satisfactory. Some of them are fairly effective but produce significantly harmful side effects, and others have inadequate effectiveness, so that they are required to be administered in large doses.

The present inventors have found a group of novel compounds which are effective as cholesterol-lowering agents and which are substantially nontoxic.

It is therefore an object of the present invention to provide a cholesterol- or lipid-lowering agents.

Another object is to provide a process for preparing cholesterol- or lipid-lowering agents.

A further object is to provide pharmaceutical compositions containing such agents.

Other objects will be apparent from the following description.

In order to accomplish the above objects, the present invention provides novel phenoxyaliphatic carboxylic acid derivatives of the formula,

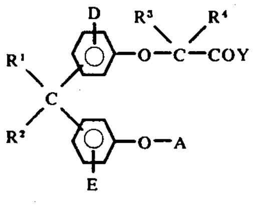

(I)

wherein $R^1$ and $R^2$ each represents hydrogen, $C_1$-$C_8$ alkyl, unsubstituted or substituted phenyl, naphthyl, benzyl, or phenethyl, or $R^1$ and $R^2$ may form unsubstituted or substituted cycloalkylidene together with a carbon atom bonded therewith; $R^3$ and $R^4$ each is hydrogen or $C_1$-$C_4$ alkyl; Y is hydroxyl, $C_1$-$C_4$ alkoxy, phenoxy, or amine residue of the formula,

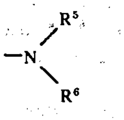

wherein $R^5$ and $R^6$ each is hydrogen, $C_1$-$C_4$ alkyl, unsubstituted- or halogen-, alkyl- or alkoxy-substituted phenyl, unsubstituted- or halogen-, alkyl- or alkoxy-substituted aralyl, or unsubstituted- or halogen-, alkyl- or alkoxy-substituted cycloalkyl; A represents hydrogen or a group of the formula,

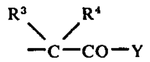

wherein $R^3$, $R^4$ and Y have the same meanings as defined above; and D and E each is hydrogen or halogen, with a proviso that $R^4$ is $C_1$-$C_4$ alkyl when both $R^1$ and $R^2$ are methyl.

In the present invention, the terms "unsubstituted or halogen-, alkyl- or alkoxy-substituted phenyl" means a group of the formula,

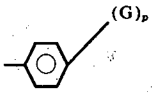

wherein G is hydrogen, halogen, $C_1$-$C_4$ alkyl or $C_1$-$C_4$ alkoxy, and p is an integer of 1–5, and the term "unsubstituted or halogen-, alkyl- or alkoxy-substituted aralkyl" means a group of the formula,

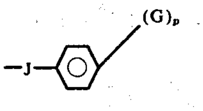

wherein J is lower alkylene, benzylidene or phenethylidene, and G and p have the same meanings as defined above, the term "unsubstituted or halogen-, alkyl- or alkoxy-substituted cycloalkyl" means a group of the formula,

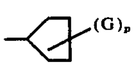 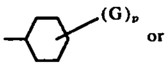 or 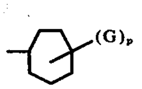

wherein G and p have the same meanings as defined above, and the term "unsubstituted or substituted cycloalkylidene" formed by $R^1$ and $R^2$ together with a carbon atom bonded therewith means a group of the formula,

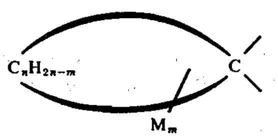

wherein M is halogen, lower alkyl, phenyl, naphthyl or alkoxy, *m* is 0 or an integer of 1–5, and *n* is an integer of 3–8.

Examples of the alkyl of $R^3$, $R^4$, $R^5$, $R^6$, G and M include methyl, ethyl, n-propyl, i-propyl, n-butyl, i-butyl and t-butyl, and examples of the alkoxy of Y, G and M include methoxy, ethoxy, n-propoxy, i-propoxy, n-butoxy, i-butoxy and t-butoxy, and examples of the lower alkylene of J include methylene, ethylene, n-propylene and i-propylene, and examples of the halogen of D, E, G and M include fluorine, chlorine, bromine and iodine.

These phenoxyaliphatic carboxylic acid derivatives (I) may be prepared by any of the procedures as shown by the following reaction scheme:

Procedure 1

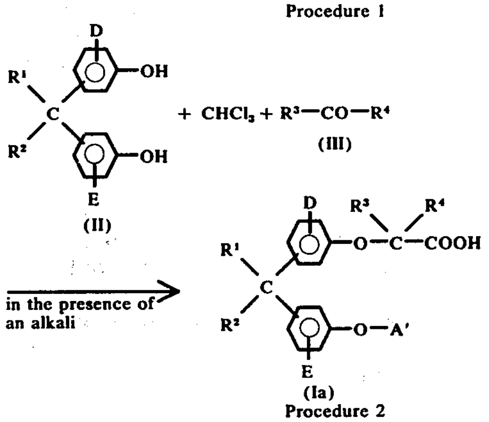

(II) (III) (Ia)

Procedure 2

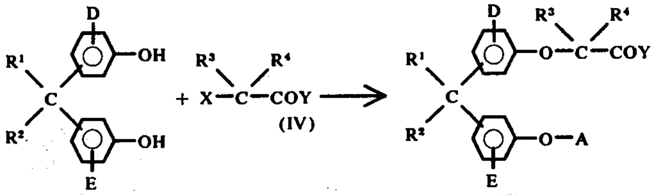

(II) (IV) (I)

Procedure 3

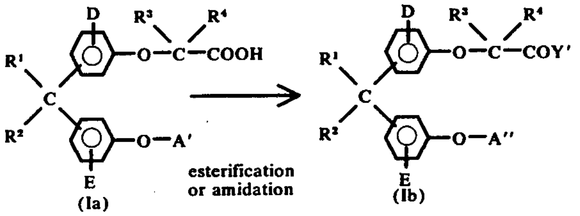

(Ia) (Ib)

wherein X is halogen or hydroxyl; A, D, E, $R^1$, $R^2$, $R^3$, $R^4$, and Y have the same meanings as defined above; A' is hydrogen or a group of the formula,

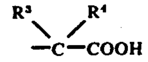

wherein $R^3$ and $R^4$ have the same meanings as defined above; A'' is hydrogen or a group of the formula,

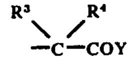

wherein $R^3$, $R^4$ and Y have the same meanings as defined above; and Y' is $C_1$-$C_4$ alkoxy, phenoxy or amine residue of the formula,

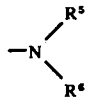

wherein $R^5$ and $R^6$ have the same meanings as defined above.

The above procedures are illustrated in detail as follows:

PROCEDURE 1

Reaction of a Bisphenol Derivative (II) with Chloroform and a Keto-Compound (III) in the Presence of an Alkali In order to carry out the reaction of this procedure, at least 1 mole of chloroform is added dropwise into a mixture containing 1 mole of a bisphenol derivative (II) and at least 1 mole of a keto-compound (III) in the presence of at least 3 moles of an alkali. Examples of the alkali used include sodium hydroxide and potassium hydroxide. The reaction requires a temperature of 20°-150° C and a reaction time of 3-40 hours. In order to obtain as the main product one of either a phenoxyaliphatic monocarboxylic acid derivative (Ia) (i.e., A' = H) or a phenoxyaliphatic dicarboxylic acid derivative (Ia)

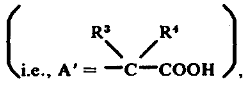

reaction conditions such as proportions of the reactants, reaction temperature and reaction time should be controlled carefully. In the case where about 1 mole of the keto-compound (III), about 1 mole of chloroform and/or about 3 moles of the alkali are used per 1 mole of the bisphenol derivative (II), a phenoxy aliphatic monocarboxylic acid derivative (Ia) (i.e., A' = H) is obtained as the main product. On the other hand, when all the keto-compound, chloroform and the alkali are used in an excessive amount, a bisphenoxyaliphatic dicarboxylic acid derivative (Ia),

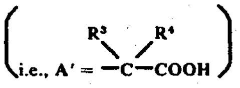

is obtained as the main product.

When a phenoxyaliphatic monocarboxylic acid derivative (Ia) (i.e., A' = H) and a phenoxyaliphatic dicarboxylic acid derivative (Ia)

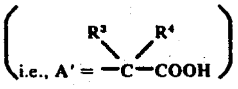

are produced at the same time, they can be separated from each other by an ordinary purification method such as recrystallization or chromatography.

The reaction may be carried out in the presence of excess chloroform and/or the keto-compound (III) or in the presence or absence of an inert reaction medium. Examples of the reaction medium include dioxane, benzene, toluene, etc.

Bisphenol derivatives of the formula (II) employed as starting material can be obtained by a method disclosed, for example, in J.A.C.S., 61, 345 (1939).

PROCEDURE 2

Condensation Reaction of a Bisphenol Derivative (II) with an α-Halogeno- or Hydroxy-Aliphatic Carboxylic Acid Derivative (IV)

In case X is halogen, 1 mole of a bisphenol derivative (II) is dissolved or suspended in an inert reaction medium and contacted with at least 1 mole of an alkaline agent to form an alkaline salt, and then at least 1 mole of an α-halogenated aliphatic acid derivative (IV) (i.e., $x$ = halogen) is added into the resultant reaction mixture to start the condensation reaction. After the reaction is over, the reaction mixture is treated according to an ordinary after-treatment to give the desired phenoxyaliphatic carboxylic acid derivative (I). Examples of the inert reaction medium used in this process include benzene and toluene. Examples of the alkaline agent used include potassium hydroxide, sodium hydroxide, alkali metal alcoholate, alkali metal carbonates, metallic sodium, sodium hydride and organic tertiary amines such as trimethylamine, triethylamine and pyridine. The reaction requires a temperature of 20°–120° C.

In order to obtain mainly one of either a phenoxyaliphatic monocarboxylic acid derivative (I) (i.e., A = H) or a phenoxyaliphatic dicarboxylic acid derivative (I)

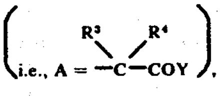, reaction conditions such as proportions of the reactants, reaction temperature and reaction time should be controlled carefully. If the alkaline agent and/or the α-halogeno-aliphatic acid derivative (IV) are used in an equimolar amount of the bisphenol derivative (II), a phenoxyaliphatic monocarboxylic acid derivative (I) (i.e., A = H) is mainly obtained. On the other hand, if both the alkaline agent and the α-halogeno-aliphatic acid derivative (IV) are used in an amount not less than 2 moles per mole of the bisphenol derivative (II), a phenoxyaliphatic dicarboxylic acid derivative (I)

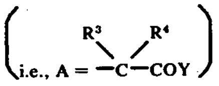

is mainly obtained.

In case X is a hydroxyl group, 1 mole of a bisphenol derivative (II) is contacted with at least 1 mole of an α-hydroxyaliphatic acid derivative (IV) (i.e., X = OH) in the presence of an acidic catalyst such as sulfuric acid, p-toluene sulfonyl chloride, arsenic acid, boric acid, sodium hydrogensulfate, potassium hydrogensulfate, etc. in the presence or absence of an inert reaction medium. Examples of the reaction medium used include benzene, toluene, dioxane, etc. The acid catalyst is used in an amount of 0.01–0.5 mole per 1 mole of a bisphenol derivative. The reaction requires a temperature of 10°–90° C.

In order to obtain mainly one of either of phenoxyaliphatic monocarboxylic acid derivative (I) (i.e. A = H) or a phenoxy-aliphatic dicarboxylic acid derivative (I)

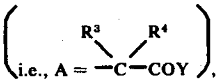, as described above, reaction conditions such as proportions of the reactants, reaction temperature and reaction time should be controlled carefully.

PROCEDURE 3

Esterification or Amidation of a Phenoxyaliphatic Acid Derivative (Ia)

A phenoxyaliphatic carboxylic acid derivative (Ia) or its reactive ester is converted into an ester or amide (Ib) by ordinary esterification or amidation procedures, for example by treatment with an esterifying agent or an amine compound or ammonia. In this process, the term "reactive ester" of the phenoxyaliphatic carboxylic acid derivative (Ia) means an acyl halide, an intramolecular acid anhydride, an ester of the acid, a salt of the acid, etc. and the term "esterification agent" means an alcohol, phenol, diazomethane, a dialkyl sulfate, an alkyl halide, an alkylhalogenosulfite, etc.

Esterification (or amidation) of a phenoxyaliphatic monocarboxylic acid derivative (Ia) (i.e., A' = hydrogen) gives only a monoester (or a monoamide) derivative (Ib) (i.e., A'' = hydrogen atom), however, esterification (or amidation) of a phenoxyaliphatic dicarboxylic acid derivative (Ia)

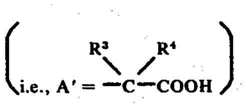

give a diester (or a diamide) derivative (Ib)

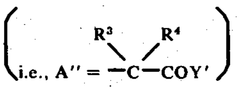

and a monoester (or a monoamide) derivative (Ib) (i.e., A'' = H) depending upon the reaction conditions such as proportions of the reactants, reaction temperature and reaction time.

For example, a diester (Ib)

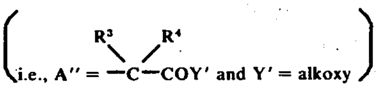

is obtained by reacting 1 mole of a phenoxyaliphatic dicarboxylic acid derivtive

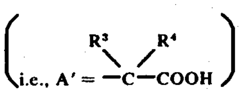

with at least 2 moles of an alcohol or at least 2 moles of diazomethane, or by reacting 1 mole of a salt of the phenoxyaliphatic dicarboxylic acid derivative with at least 2 moles of a dialkyl sulfate, an alkylhalide or an alkyl halogenosulfite, or by reacting 1 mole of an acid halide or an intramolecular acid anhydride of the phenoxyaliphatic dicarboxylic acid derivative with at least 2 moles of an alcohol or phenol. The reaction of the intramolecular acid anhydride of the phenoxyaliphatic dicarboxylic acid derivative with the alcohol or phenol may give also a monoester (Ib), (i.e., A'' = H and Y' = alkoxy or phenoxy).

The phenoxyaliphatic carboxylic acid derivative (Ia) used as a starting material of this procedure is obtained by the above-mentioned procedure 1 or procedure 2.

In the present invention, the phenoxyaliphatic carboxylic acid derivative (I) wherein Y is hydroxyl and/or A is hydrogen can be converted to a salt by treatment with an alkali. The salt is formed at the carboxyl and/or phenolic hydroxyl. An alkali metal salt can be obtained by contacting the phenoxyaliphatic carboxylic acid derivative (I) wherein Y is hydroxyl and/or A is hydrogen with sodium hydroxide, potassium hydroxide, sodium carbonate, potassium carbonate, sodium bicarbonate or ammonia, etc., or with an alcoholate of an alkali metal such as sodium methylate in an organic solvent, preferably in a lower alkanol such as methanol or ethanol, or with hydroxide, carbonate or bicarbonate of an alkali metal in an organic solvent, preferably in acetone or methanol, if necessary in the presence of a small amount of water. The alkali metal salt thus obtained can be converted to an alkaline earth metal salt by treatment with a salt of an alkaline earth metal such as calcium chloride.

According to the present invention, the following phenoxyaliphatic carboxylic acid derivatives are obtained.

Cyclo-$C_4H_6[p-C_6H_4OC(CH_3)_2CO_2H]_2$
Cyclo-$C_4H_6[p-C_6H_4OC(CH_3)_2CONH_2]_2$
Cyclo-$C_4H_6[p-C_6H_4OC(CH_3)(C_2H_5)CO_2H]_2$
Cyclo-$C_4H_6[p-C_6H_4OC(C_2H_5)_2CO_2H]_2$
3-Cl-cyclo-$C_4H_5[p-C_6H_4OC(CH_3)_2CO_2H]_2$
2-Cl-cyclo-$C_4H_5[p-C_6H_4OC(CH_3)_2CO_2H]_2$
3-$CH_3$cyclo-$C_4H_5[p-C_6H_4OC(CH_3)_2CO_2H]_2$
2-$CH_3$cyclo-$C_4H_5[p-C_6H_4OC(CH_3)_2CO_2H]_2$
3-Cl-cyclo-$C_4H_5[p-C_6H_4OC(CH_3)_2CONHC_6H_5]_2$
2-Cl-cyclo-$C_4H_5[p-C_6H_4OC(CH_3)_2CONHC_6H_{11}]_2$
3-$CH_3$-cyclo-$C_4H_5[p-C_6H_4OC(CH_3)_2CO_2C(CH_3)_3]_2$
Cyclo-$C_5H_8]p-C_6H_4OC(CH_3)_2CO_2H]_2$
Cyclo-$C_5H_8[p-C_6H_4OC(CH_3)_2CO_2C_2H_5]_2$
Cyclo-$C_5H_8[p-C_6H_4OC(CH_3)_2CO_2CH(CH_3)_2]_2$
Cyclo-$C_5H_8[p-C_6H_4OC(CH_3)_2CO_2C(CH_3)_3]_2$
Cyclo-$C_5H_8[p-C_6H_4OC(CH_3)_2CONH_2]_2$
Cyclo-$C_5H_8]p-C_6H_4OC(CH_3)_2CONHCH(CH_3)_2]_2$
Cyclo-$C_5H_8[p-C_6H_4OC(CH_3)_2CONHC_6H_5]_2$
Cyclo-$C_5H_8[p-C_6H_4OC(CH_3)_2CONHC_6H_{11}]_2$
Cyclo-$C_5H_8[p-C_6H_4OC(CH_3)_2CONHC_6H_4(4-Cl)]_2$
Cyclo-$C_5H_8[p-C_6H_4OC(CH_3)_2CONHC_6H_4(4-CH_3)]_2$
Cyclo-$C_5H_8[p-C_6H_4OC(CH_3)_2CONHC_6H_{10}4-Cl)]_2$
Cyclo-$C_5H_8[p-C_6H_4OC(CH_3)_2CONHC_6H_4(4-t-Bu)]_2$
Cyclo-$C_5H_8[p-C_6H_4OC(CH_3)(C_2H_5)CO_2H]_2$
Cyclo-$C_5H_8[p-C_6H_4OC(CH_3)(C_2H_5)CO_2C_2H_5]_2$
Cyclo-$C_5H_8[p-C_6H_4OC(C_2H_5)(C_2H_5)CO_2H]_2$
3-$CH_3$cyclo-$C_5H_7[p-C_6H_4OC(CH_3)_2CO_2H]_2$
3-$C_2H_5$-cyclo-$C_5H_7[p-C_6H_4OC(CH_3)_2CO_2H]_2$
3-t-bu-cyclo-$C_5H_7[p-C_6H_4OC(CH_3)_2CO_2H]_2$
3-Cl-cyclo-$C_5H_7[p-C_6H_4OC(CH_3)_2CO_2H]_2$
3-F-cyclo-$C_5H_7[p-C_6H_4OC(CH_3)_2CO_2H]_2$
3-I-cyclo-$C_5H_7[p-C_6H_4OC(CH_3)_2CO_2H]_2$
3-$CH_3O$-cyclo-$C_5H_7[p-C_6H_4OC(CH_3)_2CO_2H]_2$
2-Cl-cyclo-$C_5H_7[p-C_6H_4OC(CH_3)_2CO_2H]_2$
3-$CH_3$-cyclo-$C_5H_7[p-C_6H_4OC(CH_3)(C_2H_5)CO_2H]_2$
2-$CH_3$-cyclo-$C_5H_7[p-C_6H_4OC(CH_3)(C_2H_5)CO_2H]_2$
3-Cl-cyclo-$C_5H_7[p-C_6H_4OC(CH_3)(C_2H_5)CO_2H]_2$
3-$CH_3O$-cyclo-$C_5H_7[p-C_6H_4OC(CH_3)(C_2H_5)CO_2H]_2$
3-$CH_3$-cyclo-$C_5H_7[p-C_6H_4OC(C_2H_5)_2CO_2H]_2$
3-Cl-cyclo-$C_5H_7[p-C_6H_4OC(C_2H_5)_2CO_2H]_2$
3-$CH_3O$-cyclo-$C_5H_7[p-C_6H_4OC(C_2H_5)_2CO_2H]_2$
2-Cl-cyclo-$C_5H_7[p-C_6H_4OC(C_2H_5)_2CO_2H]_2$
2,3-di-Cl-cyclo-$C_5H_6[p-C_6H_4OC(CH_3)_2CO_2H]_2$
2,3-di-$CH_3$-cyclo-$C_5H_6[p-C_6H_4OC(CH_3)_2CO_2H]_2$
3,4-di-Cl-cyclo-$C_5H_6[p-C_6H_4OC(CH_3)_2CO_2H]_2$
3,5-di-$CH_3O$-cyclo-$C_5H_6[p-C_6H_4OC(CH_3)_2CO_2H]_2$
2-Cl-3-$CH_3$-cyclo-$C_5H_6[p-C_6H_4OC(CH_3)_2CO_2H]_2$
3-$CH_3O$-4-Cl-cyclo-$C_5H_6[p-C_6H_4OC(CH_3)_2CO_2H]_2$
Cyclo-$C_6H_{10}[p-C_6H_4OC(CH_3)_2CO_2H]_2$
Cyclo-$C_6H_{10}[p-C_6H_4OC(CH_3)_2CO_2C_2H_5]_2$
Cyclo-$C_6H_{10}[p-C_6H_4OC(CH_3)_2CO_2CH(CH_3)_2]_2$
Cyclo-$C_6H_{10}[p-C_6H_4OC(CH_3)_2CO_2C(CH_3)_3]_2$
Cyclo-$C_6H_{10}[p-C_6H_4OC(CH_3)_2CONH_2]_2$
Cyclo-$C_6H_{10}[p-C_6H_4OC(CH_3)_2CONHCH(CH_3)_2]_2$
Cyclo-$C_6H_{10}[p-C_6H_4OC(CH_3)_2CONHC_6H_5]_2$
Cyclo-$C_6H_{10}[p-C_6H_4OC(CH_3)_2CONHC_6H_{11}]_2$
Cyclo-$C_6H_{10}[p-C_6H_4OC(CH_3)_2CONHC_6H_4(4-Cl)]_2$
Cyclo-$C_6H_{10}[p-C_6H_4OC(CH_3)_2CONHC_6H_4(4-CH_3)]_2$
Cyclo-$C_6H_{10}[p-C_6H_4OC(CH_3)_2CONHC_6H_4(4-OCH_3)]_2$
Cyclo-$C_6H_{10}]p-C_6H_4OC(CH_3)_2CONHC_6H_{10}(4-Cl)]_2$
Cyclo-$C_6H_{10}[p-C_6H_4OC(CH_3)(C_2H_5)CO_2H]_2$
CyclO-$C_6H_{10}]p-C_6H_4OC(C_2H_5)_2CO_2H]_2$
4-$CH_3$-cyclo-$C_6H_9[p-C_6H_4OC(CH_3)_2CO_2H]_2$
Cyclo-$C_7H_{12}[p-C_6H_4OC(CH_3)_2CONH_2]_2$
Cyclo-$C_{712}[p-C_6H_4OC(CH_3)(C_2H_5)CO_2H]_2$
2-Cl-cyclo-$C_7H_{11}[p-C_6H_4OC(CH_3)_2CO_2H]_2$
3,4-di-Cl-cyclo-$C_7H_{10}[p-C_6H_4OC(CH_3)_2CO_2H]_2$
4-Cl-cyclo-$C_7H_{11}[p-C_6H_4OC(CH_3)_2CO_2H]_2$
2-$CH_3$-cyclo-$C_7H_{11}[p-C_6H_4OC(CH_3)_2CO_2H]_2$
3,4-di-$CH_3$-cyclo-$C_7H_{10}[p-C_6H_4OC(CH_3)_2CO_2H]_2$
4-$CH_3$-cyclo-$C_7H_{11}[p-C_6H_4OC(CH_3)_2CO_2H]_2$
3,4-di-$CH_3O$-cyclo-$C_7H_{10}[p-C_6H_4OC(CH_3)_2CO_2H]_2$
4-$CH_3O$-cyclo-$C_7H_{11}[p-C_6H_4OC(CH_3)_2CO_2H]_2$
Cyclo-$C_8H_{14}[p-C_6H_4OC(CH_3)_2CO_2H]_2$
Cyclo-$C_8H_{14}[p-C_6H_4OC(CH_3)_2CO_2C_2H_5]_2$
Cyclo-$C_8H_{14}[p-C_6H_4OC(CH_3)_2CONH_2]_2$
Cyclo-$C_8H_{14}[p-C_6H_4OC(CH_3)(C_2H_5)CO_2H]_2$
3-Cl-cyclo-$C_8H_{13}[p-C_6H_4OC(CH_3)_2CO_2H]_2$
4-$CH_3$-cyclo-$C_8H_{13}[p-C_6h_4OC(CH_3)_2CO_2H]_2$ $4\text{-}CH_3O\text{-}cyclo\text{-}C_8H_{13}[p\text{-}C_6H_4OC(CH_3)_2CO_2H]_2$
$Cyclo\text{-}C_9H_{16}]p\text{-}C_6H_4OC(CH_3)_2CO_2H]_2$
$Cyclo\text{-}C_9H_{16}[p\text{-}C_6H_4OC(CH_3)_2CO_2C_2H_5]_2$
$Cyclo\text{-}C_6H_{10}[p\text{-}C_6H_4OCH_2COOC_2H_5]_2$
$4\text{-}CH_3\text{-}cyclo\text{-}C_6H_9[p\text{-}C_6H_4OCH_2COOC_2H_5]_2$
$Cyclo\text{-}C_4H_6[p\text{-}C_6H_4OC(CH_3)(C_2H_5)CO_2C_2H_5]_2$
$Cyclo\text{-}C_4H_6[p\text{-}C_6H_4OC(C_2H_5)_2CO_2C_2H_5]_2$
$3\text{-}Cl\text{-}cyclo\text{-}C_4H_5[p\text{-}C_6H_4OC(CH_3)_2CO_2C_2H_5]_2$
$2\text{-}Cl\text{-}cyclo\text{-}C_4H_5[p\text{-}C_6H_4OC(CH_3)_2CO_2C_2H_5]_2$
$3\text{-}CH_3\text{-}cyclo\text{-}C_4H_5[p\text{-}C_6H_4OC(CH_3)_2CO_2C_2H_5]_2$
$2\text{-}CH_3\text{-}cyclo\text{-}C_4H_5[p\text{-}C_6H_4OC(CH_3)_2CO_2C_2H_5]_2$
$3\text{-}CH_3\text{-}cyclo\text{-}C_5H_7[p\text{-}C_6H_4OC(CH_3)_2CO_2C_2H_5]_2$
$3\text{-}C_2H_5\text{-}cyclo\text{-}C_5H_7[p\text{-}C_6H_4OC(CH_3)_2CO_2C_2H_5]_2$
$3\text{-}t\text{-}Bu\text{-}cyclo\text{-}C_5H_7[p\text{-}C_6H_4OC(CH_3)_2CO_2C_2H_5]_2$
$3\text{-}Cl\text{-}cyclo\text{-}C_5H_7[p\text{-}C_6H_4OC(CH_3)_2CO_2C_2H_5]_2$
$3\text{-}F\text{-}cyclo\text{-}C_5H_7[p\text{-}C_6H_4OC(CH_3)_2CO_2C_2H_5]_2$
$3\text{-}I\text{-}cyclo\text{-}C_5H_7[p\text{-}C_6H_4OC(CH_3)_2CO_2C_2H_5]_2$
$3\text{-}CH_3O\text{-}cyclo\text{-}C_5H_7[p\text{-}C_6H_4OC(CH_3)_2CO_2C_2H_5]_2$
$2\text{-}Cl\text{-}cyclo\text{-}C_5H_7[p\text{-}C_6H_4OC(CH_3)_2CO_2C_2H_5]_2$
$3\text{-}CH_3\text{-}cyclo\text{-}C_5H_7[p\text{-}C_6H_4OC(CH_3)(C_2H_5)CO_2C_2H_5]_2$
$2\text{-}CH_3\text{-}cyclo\text{-}C_5H_7[p\text{-}C_6H_4OC(CH_3)(C_2H_5)CO_2C_2H_5]_2$
$3\text{-}Cl\text{-}cyclo\text{-}C_5H_7[p\text{-}C_6H_4OC(CH_3)(C_2H_5)CO_2C_2H_5]_2$
$3\text{-}CH_3O\text{-}cyclo\text{-}C_5H_7[p\text{-}C_6H_4OC(CH_3)(C_2H_5)CO_2C_2H_5]_2$
$3\text{-}CH_3\text{-}cyclo\text{-}C_5H_7[p\text{-}C_6H_4OC(C_2H_5)_2CO_2C_2H_5]_2$
$3\text{-}Cl\text{-}cyclo\text{-}C_5H_7[p\text{-}C_6H_4OC(C_2H_5)_2CO_2C_2H_5]_2$
$3\text{-}CH_3O\text{-}cyclo\text{-}C_5H_7[p\text{-}C_6H_4OC(C_2H_5)_2CO_2C_2H_5]_2$
$2\text{-}Cl\text{-}cyclo\text{-}C_5H_7[p\text{-}C_6H_4OC(C_2H_5)_2CO_2C_2H_5]_2$
$2,3\text{-}di\text{-}Cl\text{-}cyclo\text{-}C_5H_6[p\text{-}C_6H_4OC(CH_3)_2CO_2C_2H_5]_2$
$2,3\text{-}di\text{-}CH_3\text{-}cyclo\text{-}C_5H_6[p\text{-}C_6H_4OC(CH_3)_2CO_2C_2H_5]_2$
$3,4\text{-}di\text{-}Cl\text{-}cyclo\text{-}C_5H_6[p\text{-}C_6H_4OC(CH_3)_2CO_2C_2H_5]_2$
$3,5\text{-}di\text{-}CH_3O\text{-}cyclo\text{-}C_5H_6[p\text{-}C_6H_4OC(CH_3)_2CO_2C_2H_5]_2$
$2\text{-}Cl\text{-}3\text{-}CH_3\text{-}cyclo\text{-}C_5H_6[p\text{-}C_6H_4OC(CH_3)_2CO_2C_2H_5]_2$
$3\text{-}CH_3O\text{-}4\text{-}Cl\text{-}cyclo\text{-}C_5H_6[p\text{-}C_6H_4OC(CH_3)_2CO_2C_2H_5]_2$
$Cyclo\text{-}C_6H_{10}[p\text{-}C_6H_4OC(CH_3)_2CONHCH(CH_2C_6H_5)C_6H_5]_2$
$4\text{-}CH_3\text{-}cyclo\text{-}C_6H_9[p\text{-}C_6H_4OC(CH_3)_2CO_2C_2H_5]_2$
$4\text{-}Cl\text{-}cyclo\text{-}C_6H_9[p\text{-}C_6H_4OC(CH_3)_2CO_2C_2H_5]_2$
$4\text{-}CH_3O\text{-}cyclo\text{-}C_6H_9[p\text{-}C_6H_4OC(CH_3)_2CO_2C_2H_5]_2$
$2\text{-}Cl\text{-}cyclo\text{-}C_6H_9[p\text{-}C_6H_4OC(CH_3)_2CO_2C_2H_5]_2$
$2\text{-}C_6H_5\text{-}cyclo\text{-}C_6H_9[p\text{-}C_6H_4OC(CH_3)_2CO_2C_2H_5]_2$
$4\text{-}C_6H_5\text{-}cyclo\text{-}C_6H_9[p\text{-}C_6H_4OC(CH_3)_2CO_2C_2H_5]_2$
$2\text{-}C_{10}H_7\text{-}cyclo\text{-}C_6H_9[p\text{-}C_6H_4OC(CH_3)_2CO_2C_2H_5]_2$
$4\text{-}C_{10}H_7\text{-}cyclo\text{-}C_6H_9[p\text{-}C_6H_4OC(CH_3)_2CO_2C_2H_5]_2$
$Cyclo\text{-}C_7H_{12}[p\text{-}C_6H_4OC(CH_3)(C_2H_5)CO_2C_2H_5]_2$
$2\text{-}Cl\text{-}cyclo\text{-}C_7H_{11}[p\text{-}C_6H_4OC(CH_3)_2CO_2C_2H_5]_2$
$3,4\text{-}di\text{-}Cl\text{-}cyclo\text{-}C_7H_{10}[p\text{-}C_6H_4OC(CH_3)_2CO_2C_2H_5]_2$
$4\text{-}Cl\text{-}cyclo\text{-}C_7H_{11}[p\text{-}C_6H_4OC(CH_3)_2CO_2C_2H_5]_2$
$2\text{-}CH_3\text{-}cyclo\text{-}C_7H_{11}[p\text{-}C_6H_4OC(CH_3)_2CO_2C_2H_5]_2$
$4\text{-}CH_3\text{-}cyclo\text{-}C_7H_{11}[p\text{-}C_6H_4OC(CH_3)_2CO_2C_2H_5]_2$
$3,4\text{-}di\text{-}CH_3O\text{-}cyclo\text{-}C_7H_{10}[p\text{-}C_6H_4OC(CH_3)_2CO_2C_2H_5]_2$
$4\text{-}CH_3O\text{-}cyclo\text{-}C_7H_{11}[p\text{-}C_6H_4OC(CH_3)_2CO_2C_2H_5]2$
$CH_2[p\text{-}C_6H_4OC(CH_3)_2CO_2H]_2$
$CH_2[p\text{-}C_6H_4OC(CH_3)_2CO_2C_2H_5]_2$
$CH_2[p\text{-}C_6H_4OC(CH_3)_2CONH_2]_2$
$CH_2[p\text{-}C_6H_4OC(CH_3)_2CONHCH(CH_3)_2]_2$
$CH_2[p\text{-}C_6H_4OC(CH_3)(C_2H_5)CO_2H]_2$
$CH_2[p\text{-}C_6H_4OC(C_2H_5)(C_2H_5)CO_2H]_2$
$CH_2[p\text{-}C_6H_4OC(CH_3)(C_2H_5)CO_2C_2H_5]_2$

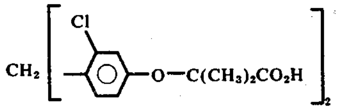

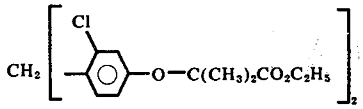

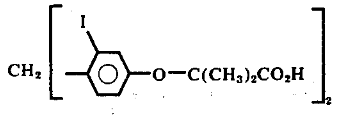

$CH_3CH[p\text{-}C_6H_4OC(CH_3)_2CO_2H]_2$
$(CH_3)_2C[p\text{-}C_6H_4OC(CH_3)_2CO_2H]_2$
$(CH_3)_2C[p\text{-}C_6H_4OC(CH_3)_2CO_2C_2H_5]_2$
$(CH_3)_2C[p\text{-}C_6H_4OC(CH_3)_2CONH_2]_2$
$(CH_3)_2C[p\text{-}C_6H_4OC(CH_3)_2CO_2C(CH_3)_3]_2$
$(CH_3)_2C[p\text{-}C_6H_4OC(CH_3)_2CONHCH_2CH_2CH_3]_2$
$(CH_3)_2C[p\text{-}C_6H_4OC(CH_3)(C_2H_5)CO_2H]_2$
$(CH_3)_2C[p\text{-}C_6H_4OC(CH_3)(C_2H_5)CO_2C_2H_5]_2$
$(CH_3)_2C[p\text{-}C_6H_4OC(CH_3)(C_2H_5)CONH_2]_2$
$(CH_3)_2C[p\text{-}C_6H_4OC(C_2H_5)_2CO_2H]_2$

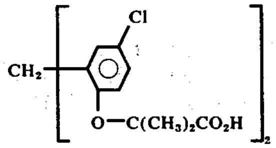

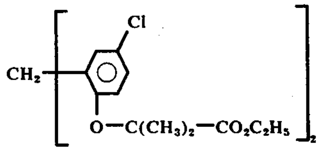

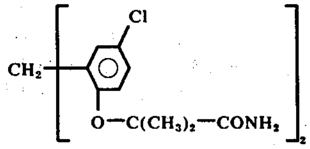

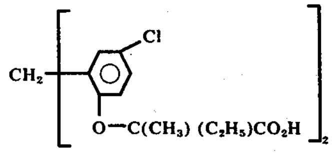

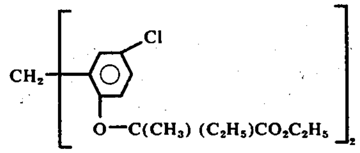

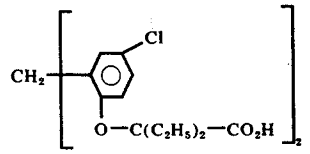

-continued

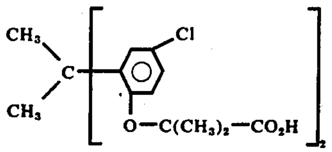

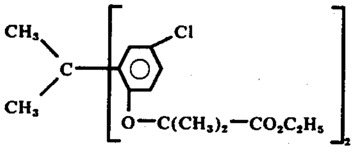

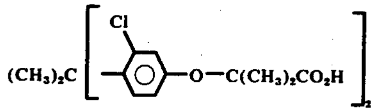

$(CH_3)(C_2H_5)C[p\text{-}C_6H_4OC(CH_3)_2CO_2H]_2$
$(CH_3)(C_2H_5)C[p\text{-}C_6H_4OC(CH_3)_2CO_2C_2H_5]_2$
$(CH_3)(C_2H_5)C[p\text{-}C_6H_4OC(CH_3)_2CONH_2]_2$
$(CH_3)(C_2H_5)C[p\text{-}C_6H_4OC(CH_3)(C_2H_5)CO_2H]_2$
$(C_2H_5)_2C[p\text{-}C_6H_4OC(CH_3)_2CO_2H]_2$
$(C_2H_5)_2C[p\text{-}C_6H_4OC(CH_3)_2CONH_2]_2$
$(C_2H_5)_2C[p\text{-}C_6H_4OC(CH_3)(C_2H_5)CO_2H]_2$
$(C_2H_5)_2C[p\text{-}C_6H_4OC(C_2H_5)_2CO_2H]_2$

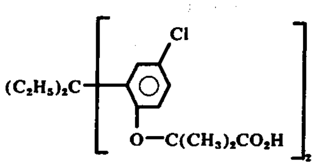

$(CH_3)(CH_2CH_2CH_3)C[p\text{-}C_6H_4OC(CH_3)_2CO_2H]_2$
$(CH_3)(CH_2CH_2CH_3)C[p\text{-}C_6H_4OC(CH_3)_2CO_2C_2H_5]_2$
$(CH_3)(CH_2CH_2CH_3)C[p\text{-}C_6H_4OC(CH_3)(C_2H_5)CO_2H]_2$

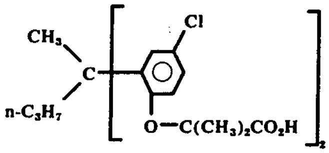

$(C_2H_5)(CH_2CH_2CH_3)C[p\text{-}C_6H_4OC(CH_3)_2CO_2H]_2$
$(C_2H_5)(CH_2CH_2CH_3)C[p\text{-}C_6H_4OC(CH_3)_2CO_2C_2H_5]_2$
$(C_2H_5)(CH_2CH_2CH_3)C[p\text{-}C_6H_4OC(CH_3)_2CONH_2]_2$
$(C_2H_5)(CH_2CH_2CH_3)C[p\text{-}C_6H_4OC(CH_3)(C_2H_5)CO_2H]_2$

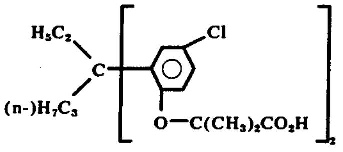

$(CH_3CH_2CH_2)_2C[p\text{-}C_6H_4OC(CH_3)_2CO_2H]_2$
$(CH_3CH_2CH_2)_2C[p\text{-}C_6H_4OC(CH_3)_2CO_2C_2H_5]_2$
$(CH_3CH_2CH_2)_2C[p\text{-}C_6H_4OC(CH_3)(C_2H_5)CO_2H]_2$

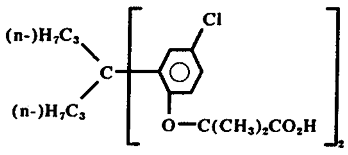

$(CH_3)[CH_3(CH_2)_3]C[p\text{-}C_6H_4OC(CH_3)_2CO_2H]_2$
$(CH_3)[CH_3(CH_2)_3]C[p\text{-}C_6H_4OC(CH_3)_2CO_2C_2H_5]_2$
$(CH_3)[CH_3(CH_2)_3]C[p\text{-}C_6H_4OC(CH_3)_2CONHCH(CH_3)_2]_2$
$(CH_3)[CH_3(CH_2)_3]C[p\text{-}C_6H_4OC(CH_3)(C_2H_5)CO_2H]_2$
$(CH_3)[CH_3(CH_2)_3]C[p\text{-}C_6H_4OC(C_2H_5)_2CO_2H]_2$

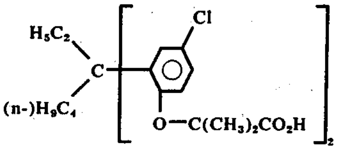

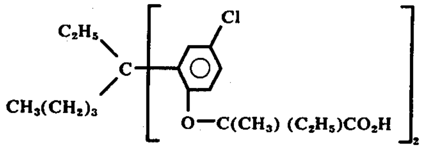

$[CH_3(CH_2)_2][CH_3(CH_2)_3]C[p\text{-}C_6H_4OC(CH_3)_2CO_2H]_2$
$[CH_3(CH_2)_2][CH_3(CH_2)_3]C[p\text{-}C_6H_4OC(CH_3)_2CO_2C_2H_5]_2$
$[CH_3(CH_2)_2][CH_3(CH_2)_3]C[p\text{-}C_6H_4OC(CH_3)_2CONHC_2H_5]_2$

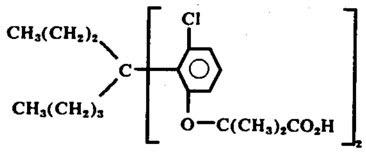

$[CH_3(CH_2)_3]_2C[p\text{-}C_6H_4OC(CH_3)_2CO_2H]2$
$[CH_3(CH_2)_3]_2C[p\text{-}C_6H_4OC(CH_3)_2CO_2C_2H_5]_2$
$[CH_3(CH_2)_3]_2C[p\text{-}C_6H_4OC(CH_3)(C_2H_5)COOH]_2$

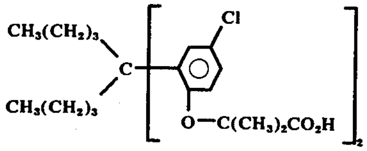

$(CH_3)[CH_3(CH_2)_4]C[p\text{-}C_6H_4OC(CH_3)_2CO_2H]_2$
$(CH_3)[CH_3(CH_2)_4]C[p\text{-}C_6H_4OC(CH_3)_2CO_2C_2H_5]_2$
$(CH_3)[CH_3(CH_2)_4]C[p\text{-}C_6H_4OC(CH_3)_2CONH_2]_2$
$(CH_3)[CH_3(CH_2)_4]C[p\text{-}C_6H_4OC(CH_3)(C_2H_5)CO_2H]_2$
$(C_2H_5)[CH_3(CH_2)_4]C[p\text{-}C_6H_4OC(CH_3)_2CO_2H]_2$
$[CH_3(CH_2)_2][CH_3(CH_2)_4]C[p\text{-}C_6H_4OC(CH_3)_2CO_2H]_2$
$[CH_3(CH_2)_3][CH_3(CH_2)_4]C[p\text{-}C_6H_4OC(CH_3)_2CO_2H]_2$
$(CH_3)[CH_3(CH_2)_5]C[p\text{-}C_6H_4OC(CH_3)_2CO_2H]_2$
$(C_2H_5)[CH_3(CH_2)_5]C[p\text{-}C_6H_4OC(CH_3)_2CO_2H]_2$
$(CH_3)[CH_3(CH_2)_6]C[p\text{-}C_6H_4OC(CH_3)_2CO_2H]_2$
$(C_2H_5)[CH_3(CH_2)_6]C[p\text{-}C_6H_4OC(CH_3)_2CO_2H]_2$
$(CH_3)[CH_3(CH_2)7]C[p\text{-}C_6H_4OC(CH_3)_2CO_2H]_2$
$(CH_3)[CH(CH_3)_2]C[p\text{-}C_6H_4OC(CH_3)_2CO_2H]_2$
$(CH_3)[CH(CH_3)(C_2H_5)]C[p\text{-}C_6H_4OC(CH_3)_2CO_2H]_2$
$[CH(CH_3)_2]_2C[p\text{-}C_6H_4OC(CH_3)_2CO_2H]_2$ $(CH_3)(C_6H_5)C[p\text{-}C_6H_4OC(CH_3)_2CO_2H]_2$
$(CH_3)(C_6H_5)C[p\text{-}C_6H_4OC(CH_3)_2CO_2C_2H_5]_2$
$(CH_3)(C_6H_5)C[p\text{-}C_6H_4OC(CH_3)_2CONH_2]_2$
$(CH_3)(C_6H_5)C[p\text{-}C_6H_4OC(CH_3)(C_2H_5)CO_2H]_2$
$(C_6H_5)_2C[p\text{-}C_6H_4OC(CH_3)_2CO_2H]_2$
$(CH_3)(C_6H_5CH_2)C[p\text{-}C_6H_4OC(CH_3)_2CO_2H]_2$
$(C_6H_5CH_2)_2C[p\text{-}C_6H_4OC(CH_3)_2CO_2H]_2$
$(C_6H_5)(C_6H_5CH_2)C[p\text{-}C_6H_4OC(CH_3)_2CO_2H]_2$
$(CH_3)(C_6H_{11})C[p\text{-}C_6H_4OC(CH_3)_2CO_2H]_2$
$(C_6H_5)(C_6H_{11})C[p\text{-}C_6H_4OC(CH_3)_2CO_2H]_2$
$(C_6H_{11})_2C[p\text{-}C_6H_4OC(CH_3)_2CO_2H]_2$
$(C_6H_{11})(C_6H_5CH_2)C[p\text{-}C_6H_4OC(CH_3)_2CO_2H]_2$
$(CH_3)(C_5H_9)C[p\text{-}C_6H_4OC(CH_3)_2CO_2H]_2$
$(CH_3)(C_7H_{13})C[p\text{-}C_6H_4OC(CH_3)_2CO_2H]_2$
$(C_6H_5)(C_5H_9)C[p\text{-}C_6H_4OC(CH_3)_2CO_2H]_2$
$(C_5H_9)(C_5H_9)C[p\text{-}C_6H_4OC(CH_3)_2CO_2H]_2$
$(C_5H_9)(C_7H_{13})C[p\text{-}C_6H_4OC(CH_3)_2CO_2H]_2$
$CH_2[p\text{-}C_6H_4OC(CH_3)_2CO_2CH_3]_2$
$CH_2[p\text{-}C_6H_4OC(CH_3)(C_2H_5)CO_2CH_3]_2$
$CH_2[p\text{-}C_6H_4OC(C_2H_5)(C_2H_5)CO_2C_2H_5]_2$

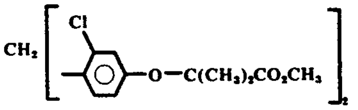

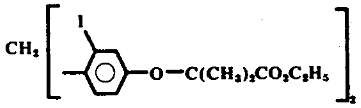

$CH_3CH[p\text{-}C_6H_4OC(CH_3)_2CO_2C_2H_5]_2$
$(CH_3)_2C[p\text{-}C_6H_4OC(CH_3)_2CO_2CH_3]_2$
$(CH_3)_2C[p\text{-}C_6H_4OC(CH_3)(C_2H_5)CO_2CH_3]_2$
$(CH_3)_2C[p\text{-}C_6H_4OC(C_2H_5)_2CO_2C_2H_5]_2$

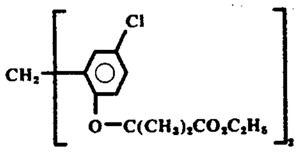

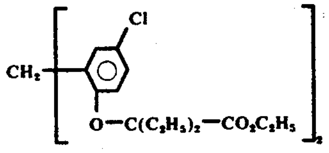

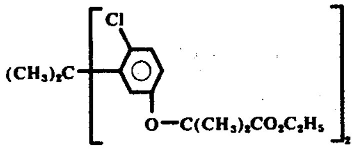

$(CH_3)(C_2H_5)C[p\text{-}C_6H_4OC(CH_3)_2CO_2CH_3]_2$
$(CH_3)(C_2H_5)C[p\text{-}C_6H_4OC(CH_3)(C_2H_5)CO_2C_2H_5]_2$

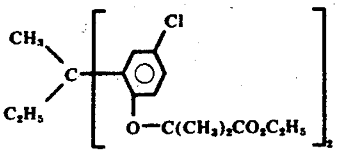

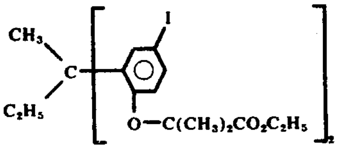

$(C_2H_5)_2C[p\text{-}C_6H_4OC(CH_3)_2CO_2CH_3]_2$
$(C_2H_5)_2C[p\text{-}C_6H_4OC(CH_3)(C_2H_5)CO_2CH_3]_2$
$(C_2H_5)_2C[p\text{-}C_6H_4OC(C_2H_5)_2CO_2C_2H_5]_2$

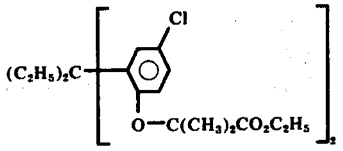

$(CH_3)(CH_2CH_2CH_3)C[p\text{-}C_6H_4OC(CH_3)_2CO_2CH_3]_2$
$(CH_3)(CH_2CH_2CH_3)C[p\text{-}C_6H_4OC(CH_3)(C_2H_5\text{-})CO_2C_2H_5]_2$

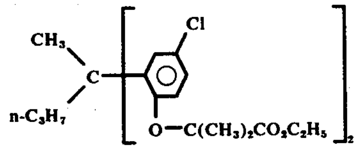

$(C_2H_5)(CH_2CH_2CH_3)C[p\text{-}C_6H_4O\text{-}C(CH_3)_2CO_2CH_3]_2$
$(C_2H_5)(CH_2CH_2CH_3)C[p\text{-}C_6H_4OC(CH_3)(C_2H_5\text{-})CO_2C_2H_5]_2$

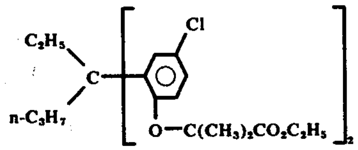

$(CH_3CH_2CH_2)_2C[p\text{-}C_6H_4OC(CH_3)_2CO_2CH_3]_2$
$(CH_3CH_2CH_2)_2C[p\text{-}C_6H_4OC(CH_3)(C_2H_5)CO_2C_2H_5]_2$

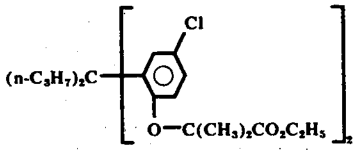

$(CH_3)[CH_3(CH_2)_3]C[p\text{-}C_6H_4OC(CH_3)_2CO_2CH_3]_2$
$(CH_3)[CH_3(CH_2)_3]C[p\text{-}C_6H_4CO(CH_3)(C_2H_5\text{-})CO_2C_2H_5]_2$
$(CH_3)[CH_3(CH_2)_3]C[p\text{-}C_6H_4OC(C_2H_5)_2CO_2C_2H_5]_2$

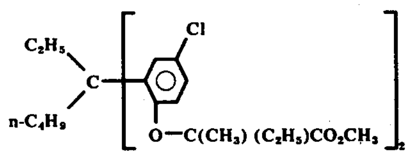

$[CH_3(CH_2)_2][CH_3(CH_2)_3]C[p\text{-}C_6H_4O\text{-}C(CH_3)_2CO_2CH_3]_2$
$[CH_3(CH_2)_2][CH_3(CH_2)_3]C[p\text{-}C_6H_4OC(CH_3)(C_2H_5\text{-})CO_2C_2H_5]_2$

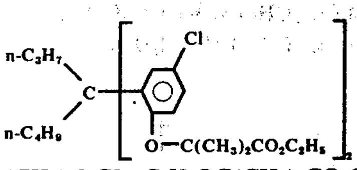

$[CH_3(CH_2)_3]_2C[p\text{-}C_6H_4OC(CH_3)_2CO_2CH_3]_2$ $[CH_3(CH_2)_3]_2C[p\text{-}C_6H_4OC(CH_3)(C_2H_5)COOC_2H_5]_2$

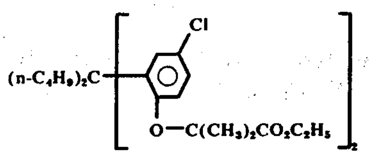

$(CH_3)[CH_3(CH_2)_4]C[p\text{-}C_6H_4OC(CH_3)_2CO_2CH_3]_2$ $(CH_3)[CH_3(CH_2)_4]C[p\text{-}C_6H_4OC(CH_3)(C_2H_5)CO_2C_2H_5]_2$ $(C_2H_5)[CH_3(CH_2)_4]C[p\text{-}C_6H_4OC(CH_3)_2CO_2C_2H_5]_2$ $[CH_3(CH_2)_2][CH_3(CH_2)_4]C[p\text{-}C_6H_4OC(CH_3)_2CO_2C_2H_5]_2$ $[CH_3(CH_2)_3][CH_3(CH_2)_4]C[p\text{-}C_6H_4OC(CH_3)_2CO_2C_2H_5]_2$ $[CH_3(CH_2)_4]_2C[p\text{-}C_6H_4OC(CH_3)_2CO_2C_2H_5]_2$ $(CH_3)[CH_3(CH_2)_5]C[p\text{-}C_6H_4OC(CH_3)_2CO_2C_2H_5]_2$ $(C_2H_5)[CH_3(CH_2)_5]C[p\text{-}C_6H_4OC(CH_3)_2CO_2C_2H_5]_2$ $[CH_3(CH_2)_2][CH_3(CH_2)_5]C[p\text{-}C_6H_4OC(CH_3)_2CO_2C_2H_5]_2$ $(CH_3)[CH_3(CH_2)_6]C[p\text{-}C_6H_4OC(CH_3)_2CO_2C_2H_5]_2$ $(C_2H_5)[CH_3(CH_2)_6]C[p\text{-}C_6H_4OC(CH_3)_2CO_2C_2H_5]_2$ $(CH_3)[CH_3(CH_2)_7]C[p\text{-}C_6H_4OC(CH_3)_2CO_2C_2H_5]_2$ $(CH_3)[CH_3(CH_2)_7]C[p\text{-}C_6H_4OC(CH_3)_2CONHCH_3]_2$ $(CH_3)[CH(CH_3)_2]C[p\text{-}C_6H_4OC(CH_3)_2CO_2C_2H_5]_2$ $(CH_3)[CH(CH_3)(C_2H_5)]C[p\text{-}C_6H_4OC(CH_3)_2CO_2C_2H_5]_2$ $[CH(CH_3)_2]_2C[p\text{-}C_6H_4OC(CH_3)_2CO_2C_2H_5]_2$ $(CH_3)(C_6H_5)C[p\text{-}C_6H_4OC(CH_3)_2CO_2CH_3]_2$ $(CH_3)(C_6H_5)C[p\text{-}C_6H_4OC(CH_3)(C_2H_5)CO_2C_2H_5]_2$ $(C_6H_5)_2C[p\text{-}C_6H_4OC(CH_3)_2CO_2C_2H_5]_2$ $(CH_3)(C_6H_5CH_2)C[p\text{-}C_6H_4OC(CH_3)_2CO_2C_2H_5]_2$ $(C_6H_5CH_2)_2C[p\text{-}C_6H_4OC(CH_3)_2CO_2C_2H_5]_2$ $(C_6H_5)(C_6H_5CH_2)C[p\text{-}C_6H_4OC(CH_3)_2CO_2C_2H_5]_2$ $(CH_3)(C_6H_{11})C[p\text{-}C_6H_4OC(CH_3)_2CO_2C_2H_5]_2$ $(C_6H_5)(C_6H_{11})C[p\text{-}C_6H_4OC(CH_3)_2CO_2C_2H_5]_2$ $(C_6H_{11})_2C[p\text{-}C_6H_4OC(CH_3)_2CO_2C_2H_5]_2$ $(C_6H_{11})(C_6H_5CH_2)C[p\text{-}C_6H_4OC(CH_3)_2CO_2C_2H_5]_2$ $(CH_3)(C_5H_9)C[p\text{-}C_6H_4OC(CH_3)_2CO_2C_2H_5]_2$ $(CH_3)(C_7H_{13})C[p\text{-}C_6H_4OC(CH_3)_2CO_2C_2H_5]_2$ $(CH_3)(C_7H_{13})C[p\text{-}C_6H_4OC(CH_3)_2CON(C_2H_5)_2]_2$ $(C_6H_3)(C_5H_9)C[p\text{-}C_6H_4OC(CH_3)_2CO_2C_2H_5]_2$ $(C_5H_9)(C_5H_9C[p\text{-}C_6H_4OC(CH_3)_2CO_2C_2H_5]_2$ $(C_5H_9)(C_7H_{13})C[p\text{-}C_6H_4OC(CH_3)_2CO_2C_2H_5]_2$

B—$CH_2COOH$

B—$CH(CH_3)COOH$

B—$CH(C_2H_5)COOH$

B—$CH(n\text{-}C_3H_7)COOH$

B—$CH(i\text{-}C_3H_7)COOH$

B—$CH(n\text{-}C_4H_9)COOH$

B—$CH(i\text{-}C_4H_9)COOH$

B—$CH(t\text{-}C_4H_9)COOH$

B—$C(CH_3)_2)COOH$

B—$C(CH_3)(C_2H_5)COOH$

B—$C(CH_3)(n\text{-}C_3H_7)COOH$

B—$C(CH_3)(i\text{-}C_3H_7)COOH$

B—$C(CH_3)(n\text{-}C_4H_9)COOH$

B—$C(CH_3)(i\text{-}C_4H_9)COOH$

B—$C(CH_3)(t\text{-}C_4H_9)COOH$

B—$C(C_2H_5)_2COOH$

B—$C(C_2H_5)(n\text{-}C_3H_7)COOH$

B—$C(C_2H_5)(i\text{-}C_3H_7)COOH$

B—$C(C_2H_5)(n\text{-}C_4H_9)COOH$

B—$C(C_2H_5)(i\text{-}C_4H_9)COOH$

B—$C(C_2H_5)(t\text{-}C_4H_9$

B—$C(n\text{-}C_3H_7)COOH$

B—$C(n\text{-}C_3H_7)(i\text{-}C_3H_7)COOH$

B—$C(n\text{-}C_3H_7)(n\text{-}C_4H_9)COOH$

B—$C(n\text{-}C_3H_7)(i\text{-}C_4H_9)COOH$

B—$C(n\text{-}C_3H_7)(t\text{-}C_4H_9)COOH$

B—$C(i\text{-}C_3H_7)_2COOH$

B—$C(i\text{-}C_3H_7)(n\text{-}C_4H_9)COOH$

B—$C(i\text{-}C_3H_7)(i\text{-}C_4H_9)COOH$

B—$C(i\text{-}C_3H_7)(t\text{-}C_4H_9)COOH$

B—$C(n\text{-}C_4H_9)_2COOH$

B—$C(n\text{-}C_4H_9)(i\text{-}C_4H_9)COOH$

B—$C(n\text{-}C_4H_9)(t\text{-}C_4H_9)COOH$

B—$C(i\text{-}C_4H_9)_2COOH$

B—$C(i\text{-}C_4H_9)(t\text{-}C_4H_9)COOH$

B—$C(t\text{-}C_4H_9)_2COOH$ $H_2C(B')p\text{-}C_6H_4OCH_2CO_2H$ $H_2C(B')p\text{-}C_6H_4OCH(CH_3)CO_2H$ $H_2C(B')p\text{-}C_6H_4OCH(C_2H_5)CO_2H$ $H_2C(B')p\text{-}C_6H_4OC(CH_3)_2CO_2H$ $H_2C(B')p\text{-}C_6H_4OC(CH_3)(C_2H_5)CO_2H$ $H_2C(B')p\text{-}C_6H_4OC(CH_3)(n\text{-or-}i\text{-}C_3H_7)CO_2H$ $H_2C(B')p\text{-}C_6H_4OC(C_2H_5)(C_2H_5)CO_2H$ $H_2C(B')p\text{-}C_6H_4OC(n\text{-or-}i\text{-}C_3H_7)(n\text{-or-}i\text{-}C_4H_9)CO_2H$ $CH_3CH(B')p\text{-}C_6H_4OCH_2CO_2H$ $CH_3CH(B')p\text{-}C_6H_4OCH(CH_3)CO_2H$ $(CH_3)_2C(B')p\text{-}C_6H_4OCH_2CO_2H$ $(CH_3)_2C(B')p\text{-}C_6H_4OCH(CH_3)CO_2H$ $(CH_3)_2C(B')p\text{-}C_6H_4OC(CH_3)_2CO_2H$ $(CH_3)_2C(B')p\text{-}C_6H_4OC(CH_3)(C_2H_5)CO_2H$ $(CH_3)(C_2H_5)C(B')p\text{-}C_6H_4OC(C_2H_5)$ $(n\text{-or-}i\text{-}C_3H_7)CO_2H$ $(CH_3)(C_2H_5)C(B')p\text{-}C_6H_4OCH_2CO_2H$ $(CH_3)$ $(C_2H_5)C(B')p\text{-}C_6H_4OC(C_2H_5)_2CO_2H$ $(C_2H_5)_2C(B')p\text{-}C_6H_4OC(CH_3)$ $(C_2H_5)CO_2H$ $(CH_3)$ $(n\text{-or-}i\text{-}C_3H_7)C(B')p\text{-}C_6H_4OC(C_2H_5)(C_2H_5)CO_2H$ $(C_2H_5)(n\text{-or-}i\text{-}C_3H_7)C(B')p\text{-}C_6H_4OC(CH_3)(n\text{-or-}i\text{-}C_3H_7)CO_2H$ $(n\text{-or-}i\text{-}C_3H_7)(n\text{-}i\text{-or-}t\text{-}C_4H_9)C(B')p\text{-}C_6H_4OC(CH_3)_2CO_2H$ $(i\text{-}C_3H_7)(n\text{-}C_4H_9)C(B')p\text{-}C_6H_4OC(CH_3)_2CO_2H$ $(CH_3)(n\text{-}C_5H_{11})C(B')p\text{-}C_6H_4OC(CH_3)_2CO_2H$ $(CH_3)(n\text{-}C_5H_{11})C(B')p\text{-}C_6H_4OC(CH_3)(C_2H_5)COOH$ $(C_2H_5)[n\text{-}CH_3(CH_2)_6]C(B')p\text{-}C_6H_4OC(CH_3)(C_2H_5)CO_2H$ There can also be prepared methyl esters, ethyl esters, n-propyl esters, iso-propyl esters, n-butyl esters, iso-butyl esters or t-butyl esters of the abovementioned monocarboxylic acids and sodium, potassium, calcium, magnesium, aluminum or ammonium salts of the aboce-mentioned monocarboxylic acids.

In the above exemplified compounds, B means a group of the formula

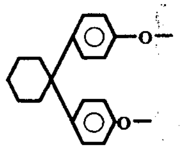

and B means a group of the formula

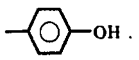

The present invention further provides a pharmaceuticl composition containing a phenoxyaliphatic carboxylic acid derivative of the formula,

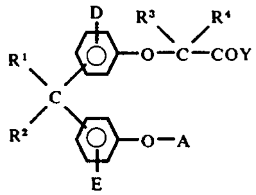

wherein $R^1$ and $R^2$ each represents hydrogen, $C_1$-$C_8$ alkyl, unsubstituted or substituted phenyl, naphthyl, benzyl, oe phenethyl, or $R^1$ and $R^2$ may form unsubstituted or substituted cycloalkylidene together with a carbon atom bonded therewith; $R^3$ and $R^4$ each is hydrogen or $C_1$-$C_4$ alkyl; Y is hydroxyl, $C_1$-$C_4$ alkoxy, phenoxy, or amine residue of the formula,

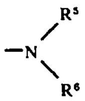

wherein $R^5$ and $R^6$ each is hydrogen, $C_1$-$C_4$ alkyl, unsubstituted- or halogen-, alkyl- or alkoxy-substituted phenyl, unsubstituted- or halogen-, alkyl- or alkoxy-substituted aralyl, or unsubstituted- or halogen-, alkyl- or alkoxysubstituted cycloalkyl; A represents hydrogen or a group of the formula,

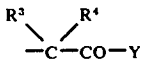

wherein $R^3$, $R_4$ and Y have the same meanings as defined above; and D and E each is hydrogen or halogen.

The cholesterol-lowering agents of this invention may be, for example, orally administered. Usually the amount orally administered is 0.01 – 10 g. per day/human adult, preferably 0.05 – 3 g, per day/human adult. The cholesterol-lowering agent may be in any suitable form which is conventional for oral administration. Thus, it may be encased in a capsule, or it may be in a liquid form, in a tablet form, or in a powder form. In preparing the agents in these various forms, the active compound may be mixed with or impregnated in a suitable solid carrier.

The process of the present invention is illustrated in more detail by the following examples, however it is not intended to limit the invention.

EXAMPLES 1 – 18

General Procedure

Into a mixture of a bishydroxyphenyl derivative and a ketone compound as added crushed potassium hydroxide or sodium hydroxide. Chloroform was added dropwise into the above mixture with stirring at 20°– 80° C, and the resultant mixture was heated at 50°– 150° C to complete the reaction. Thereafter the reaction mixture was concentrated to give a residue. Into the residue was added water. After cooling, the resultant mixture was treated with activated charcoal and acidified by diluted hydrochloric acid or sulfuric acid to give an oily substance. The oily substance was extracted by ether and the ether solution was contacted with aqueous diluted $NA_2CO_3$ solution. The separated aqueous layer was washed with ether, acidified and again extracted with ether. The obtained ether layer was dried over anhydrous sodium sulfate and concentrated to give a crude product which was purified by recrystallization or chromatography.

Results are summarized in Table 1.

TABLE 1

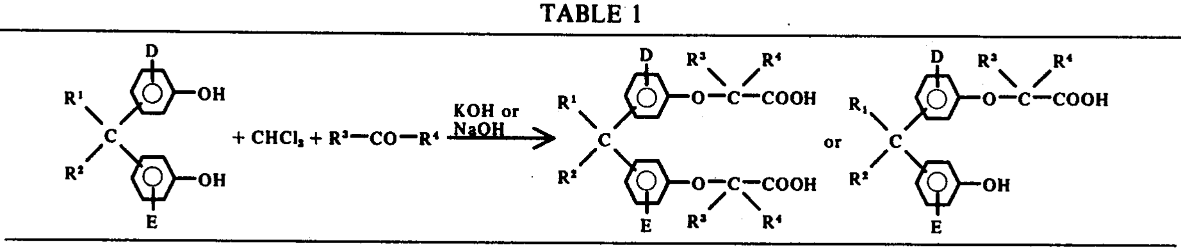

| Ex. No. | Starting Materials 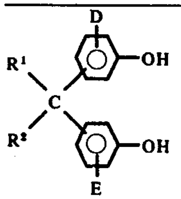 g. | $R^3$—CO—$R^4$ g | KOH or NaOH g | $CHCl_3$ g (temp.) | Reaction Time hours (temp.) | Product Chemical Structure g | Physical property | Elementary analysis Cal. (%) | Found (%) |
|---|---|---|---|---|---|---|---|---|---|
| 1 | 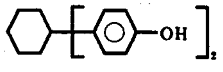 10 g | $CH_3COCH_3$ 61 g | KOH 17 g | 24 g (40° - 50° C) | 10 reflux | 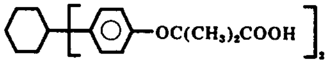 10 g | m.p. 159° - 160° C (from benzene) | C: 70.89, H: 7.32 | 71.02 7.13 |
| 2 | 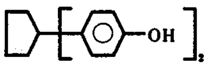 10 g | $CH_3$—CO—$CH_3$ 65 g | KOH 28.4 g | 23 g (35° - 40° C | 10 reflux | 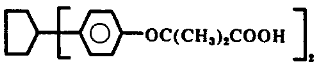 8 g | m.p. 155° - 157° C (from ether-petroleum ether) | C: 70.40, H: 7.09, | 70.63 6.97 |
| 3 | 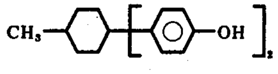 18 g | $CH_3COCH_3$ 97.2 g | KOH 47.8 g | 28 g (40° - 50° C) | 10 reflux | 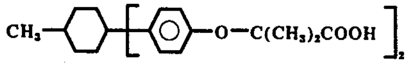 16 g | m.p. 164° - 166° C | C: 71.34, H: 7.54, | 71.13 7.50 |
| 4 | 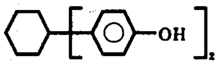 6 g | $CH_3$—CO—$C_2H_5$ 44 g | KOH 16.2 g | 12 g (35° - 45° C) | 20 reflux | 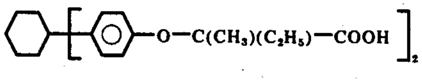 1 g | m.p. 141° - 143° C | C: 71.77, H: 7.74, | 71.56 7.71 |
| 5 | 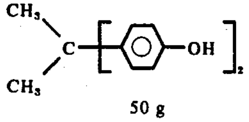 50 g | $CH_3COCH_3$ 336 g | KOH 115 g | 96.8 g (30° - 35° C) | 10 reflux | 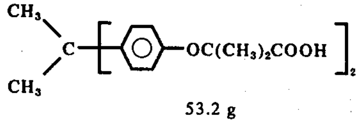 53.2 g | m.p. 142° - 142.5° C colorless crystal | C: 69.98, H: 7.05 | 70.05 7.05 |

TABLE 1-continued

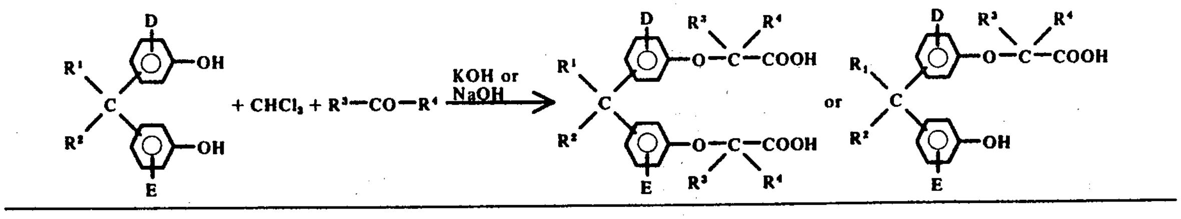

| Ex. No. | Starting Materials 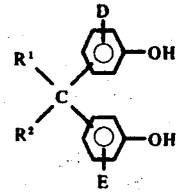 g. | Starting Materials $R^3-CO-R^4$ g | Starting Materials KOH or NaOH g | Starting Materials $CHCl_3$ g (temp.) | Reaction Time hours (temp.) | Product Chemical Structure g | Product Physical property | Product Elementary analysis Cal. (%) | Product Elementary analysis Found (%) |
|---|---|---|---|---|---|---|---|---|---|
| 6 | 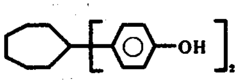 3.84 g | $CH_3-CO-CH_3$ 30 g | KOH 12.5 g | 7 g (30° - 40° C) | 9.5 reflux | 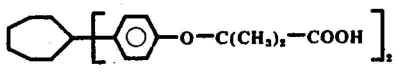 5 g | m.p. 134° - 135° C | C: 71.34, H: 7.54, | 71.49 7.83 |
| 7 | 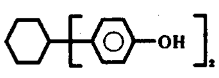 15 g | $CH_3-CO-n-C_3H_7$ 120 g | KOH 36 g | 24 g (45° - 50° C) | 35 90° C | 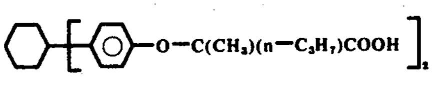 2 g | $n_D^{21}$ 1.5328 | C: 72.55, H: 8.13, | 72.37 8.31 |
| 8 | 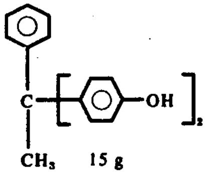 15 g | $CH_3COCH_3$ 78.8 g | KOH 38.8 g | 22.7 g (30° - 40° C) | 10 reflux | 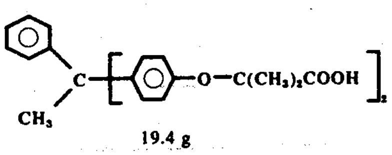 19.4 g | $n_D^{20}$ 1.5610 yellow-ish brown oil | C: 72.71 H: 6.54, | 72.72 6.37 |
| 9 | 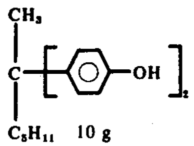 10 g | $CH_3-CO-CH_3$ 56 g | NaOH 25 g | 17 g (30° - 40° C) | 10 reflux | 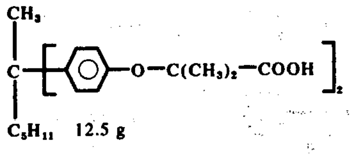 12.5 g | $n_D^{21}$ 1.5431 pale brown oil | C: 71.02, H: 7.95, | 71.25 7.96 |

TABLE 1-continued
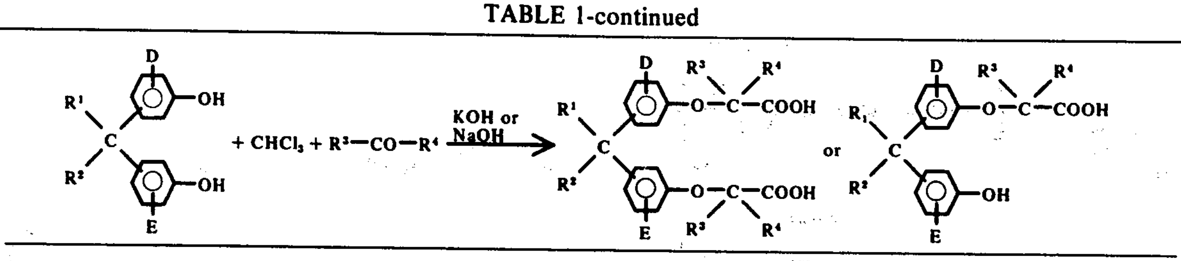
| Ex. No. | Starting Materials 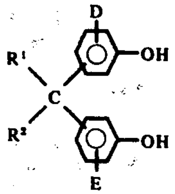 g. | R³—CO—R⁴ g | KOH or NaOH g | CHCl₃ g (temp.) | Reaction Time hours (temp.) | Product Chemical Structure g | Physical property | Elementary analysis Cal. (%) | Found (%) |
|---|---|---|---|---|---|---|---|---|---|
| 10 | 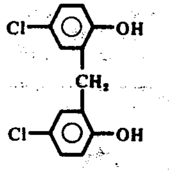 25 g | $CH_3$—CO—$CH_3$ 141.5 g | KOH 69.8 g | 40.8 g (30° - 40° C) | 8 reflux | 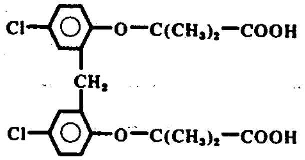 21.6 g | m.p. 173° C colorless crystal | C: 57.15, H: 5.02, Cl: 16.07, | 56.98 4.94 15.95 |
| 11 | 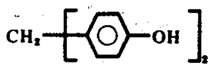 20 g | $CH_3$—CO—$CH_3$ 151.2 g | KOH 101.4 g | 47.6 g (35° - 40° C) | 7 reflux | 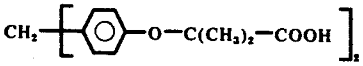 5 g | m.p. 108° - 110° C | C: 67.73, H: 6.50 | 67.78 6.74 |
| 12 | 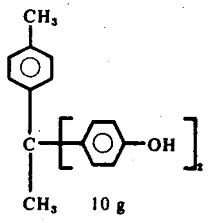 10 g | $CH_3$—CO—$CH_3$ 50.1 g | KOH 24.4 g | 14.46 g (30° - 40° C) | 8 reflux | 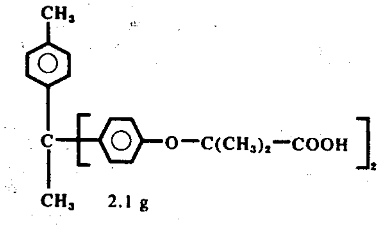 2.1 g | m.p. 165° - 166° C | C: 73.09, H: 6.77, | 72.82 7.13 |

TABLE 1-continued

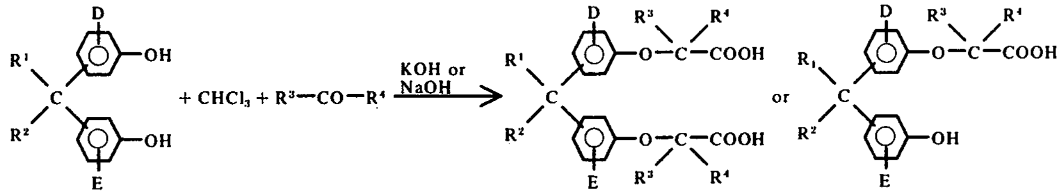

| Ex. No. | Starting Materials 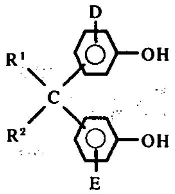 g. | Starting Materials $R^3-CO-R^4$ g | Starting Materials KOH or NaOH g | Starting Materials $CHCl_3$ g (temp.) | Reaction Time hours (temp.) | Product Chemical Structure g | Product Physical property | Product Elementary analysis Cal. (%) | Product Elementary analysis Found (%) |
|---|---|---|---|---|---|---|---|---|---|
| 13 | 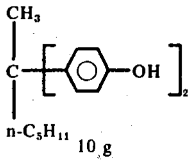 10 g | $CH_3-CO-CH_3$ 56 g | KOH 35 g | 17 g (30° – 35° C) | 7 reflux | 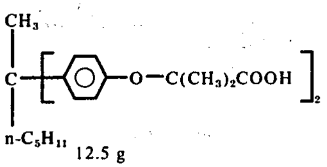 12.5 g | $n_D^{27}$ 1.5431 | C: 71.02, H: 7.95, | 71.28 7.96 |
| 14 | 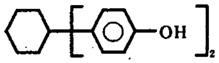 26.8 g | $CH_3COCH_3$ 100 g | KOH 32 g | 14.4 g (30° – 40° C) | 5 reflux | 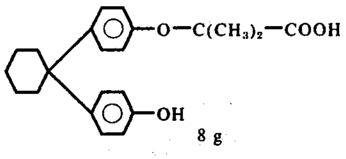 8 g | m.p. 181° – 182.5° C | C: 74.55, H: 7.39, | 74.59 7.60 |
| 15 | 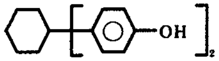 26.8 g | $CH_3COC_2H_5$ 93.6 g | KOH 32 g | 14.4 g (35° – 45° C) | 15 reflux | 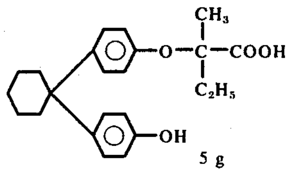 5 g | m.p. 138° – 141° C | C: 74.97, H: 7.66, | 74.84 7.62 |

TABLE 1-continued

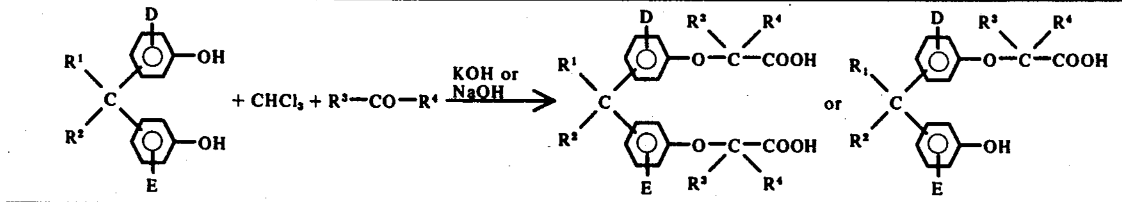

| Ex. No. | Starting Materials: 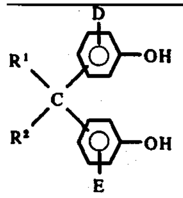 g. | Starting Materials: $R^3$—CO—$R^4$ g | KOH or NaOH g | $CHCl_3$ g (temp.) | Reaction: Time hours (temp.) | Product: Chemical Structure g | Physical property | Elementary analysis Cal. (%) | Elementary analysis Found (%) |
|---|---|---|---|---|---|---|---|---|---|
| 16 | 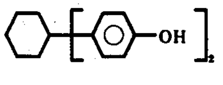 26.8 g | $CH_3$—CO—n—$C_3H_7$ 112 g | KOH 32 g | 14.4 g (35° - 45° C) | 20 90° C | 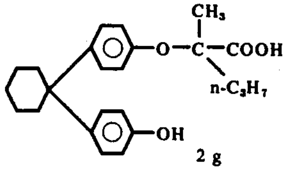 2 g | light brown resinous matter | C: 75.36, H: 7.91, | 75.53 8.09 |
| 17 | 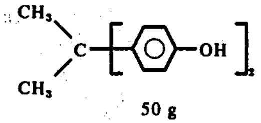 50 g | $CH_3COCH_3$ 168 g | KOH 57.7 g | 21 g (35° - 40° C) | 5 reflux | 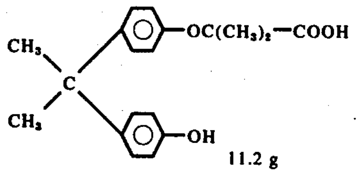 11.2 g | m.p. 132° - 135° C | C: 72.59, H: 7.05, | 72.41 7.01 |
| 18 | 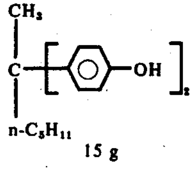 15 g | $CH_3COC_2H_5$ 170 g | KOH 20 g | 7.5 g (40° - 50° C) | 10 reflux | 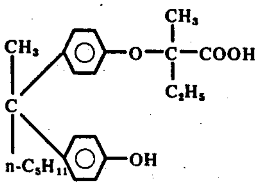 1 g | $n_D^{23}$ 1.5440 | C: 74.97, H: 8.39, | 75.29 8.50 |

EXAMPLES 19 – 29

General Procedure

Into a mixture consisting of a bis-(4-hydroxyphenyl)-derivative and dry toluene was added a toluene suspension of sodium hydride under cooling. After stirring the mixture for a short time, a mixture of an α-halogeno aliphatic acid derivative and toluene was added dropwise thereto, and heated with stirring for several hours. After cooling, the reaction mixture was washed with water. The toluene was distilled off to yield a crude produce which was purified by recrystallization or column chromatography.

Results are summarized in Table 2.

TABLE 2

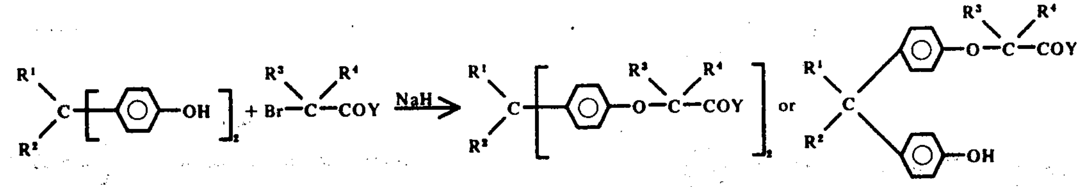

| Ex. No. | Starting Materials 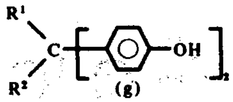 (g) | 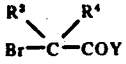 (g.) | Toluene (ml) | Reaction Temp-pera-ture (° C) | Reaction Time (hrs.) | Product Chemical Structure (g.) | Physical property | Elementary Analysis Cal. (%) Found (%) |
|---|---|---|---|---|---|---|---|---|
| 19 | 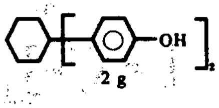 2 g | 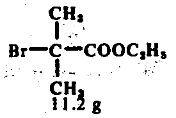 11.2 g | 20 | 60–80 | 2 | 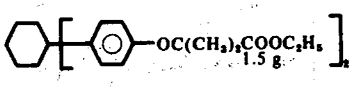 1.5 g | m.p. 103.5°–104.5° C | C: 72.55, 72.22<br>H: 8.12, 8.19 |
| 20 | 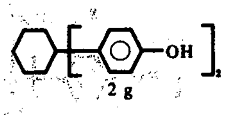 2 g | 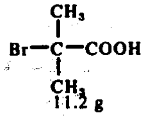 11.2 g | 20 | 60–80 | 2 | 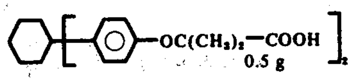 0.5 g | m.p. 159°–160° C | C: 70.89, 71.10<br>H: 7.32, 7.20 |
| 21 | 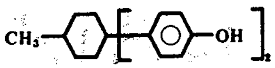 2 g | 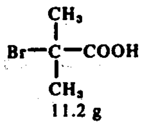 11.2 g | 20 | 60–80 | 2 | 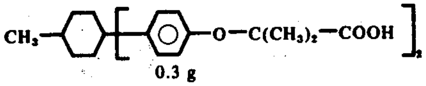 0.3 g | m.p. 164°–166° C | C: 71.34, 71.21<br>H: 7.54, 7.56 |
| 22 | 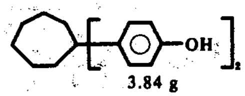 3.84 g | 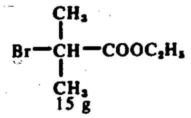 15 g | 20 | 60–80 | 2 | 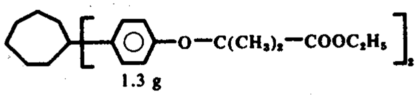 1.3 g | $n_D^{23.5}$ 1.5274 | C: 72.91, 73.11<br>H: 8.29, 8.22 |
| 23 | 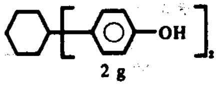 2 g | 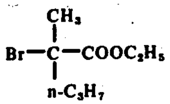 10 g | 20 | 60–80 | 2 | 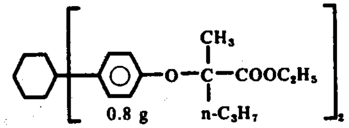 0.8 g | $n_D^{27.5}$ 1.5170 | C: 73.88, 73.63<br>H: 8.75, 8.74 |
| 24 | 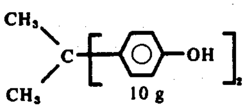 10 g | 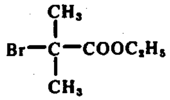 17 g | 100 | 60–80 | 2 | 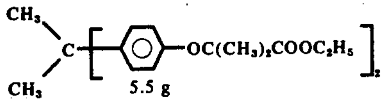 5.5 g | pale yellow oil $n_D^{22}$ 1.5233 | C: 71.02, 71.28<br>H: 7.95, 7.88 |

TABLE 2-continued
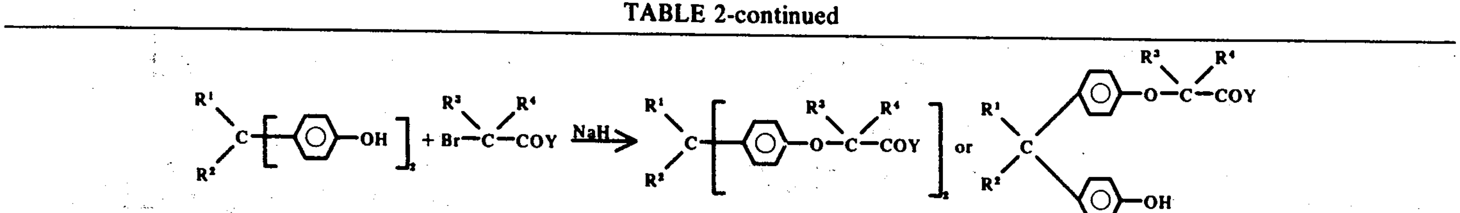
| Ex. No. | Starting Materials 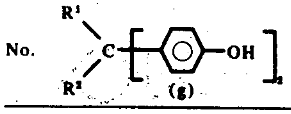 (g) | 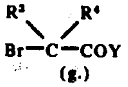 (g.) | Toluene (ml) | Reaction Temperature (°C) | Reaction Time (hrs.) | Product Chemical Structure (g.) | Physical property | Elementary Analysis Cal. (%) | Elementary Analysis Found (%) |
|---|---|---|---|---|---|---|---|---|---|
| 25 | 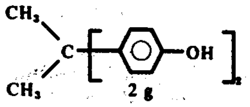 2 g | 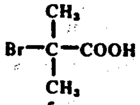 5 g | 100 | 60–80 | 2 | 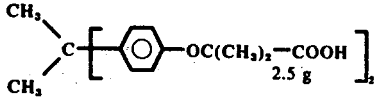 2.5 g | m.p. 141°–143° C | C: 69.98<br>H: 7.05 | 70.00<br>7.10 |
| 26 | 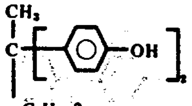 2 g | 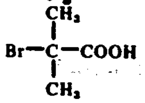 7 g | 100 | 60–80 | 2 | 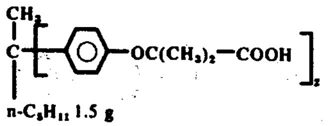 1.5 g | $n_D^{22}$ 1.5431 | C: 71.02<br>H: 7.95 | 71.31<br>7.87 |
| 27 | 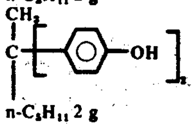 2 g | 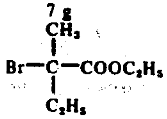 8 g | 100 | 60–80 | 2 | 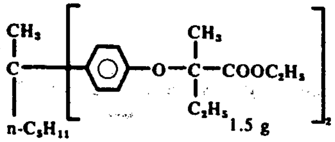 1.5 g | $n_D^{27}$ 1.5076 | C: 73.30<br>H: 8.95 | 72.81<br>8.89 |
| 28 | 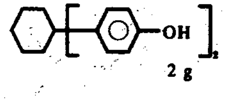 2 g | 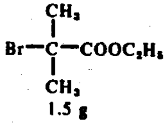 1.5 g | 20 | 70–80 | 3 | 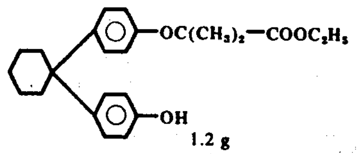 1.2 g | m.p. 117.5°–118.5° C | C: 75.36<br>H: 7.91 | 75.43<br>7.99 |
| 29 | 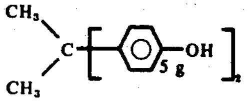 5 g | 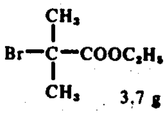 3.7 g | 80 ml. (benzene) | reflux | 2 | 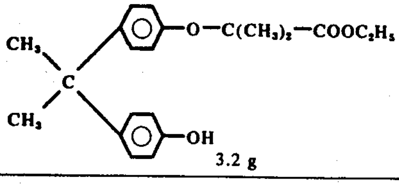 3.2 g | $n_D^{22}$ 1.5472 | C: 73.66<br>H: 7.66 | 73.56<br>7.80 |

EXAMPLES 30 - 31

General Procedure

Into a mixture containing a bis-(4'-hydroxyphenyl) derivative and ethyl α-hydroxy-isobutyrate was added 10 - 20% sulfuric acid at 20°-80° C. After the completion of the addition of sulfuric acid, the reaction mixture was stirred at the same temperature. After cooling, the reaction mixture was washed with water, and was treated with diluted sodium carbonate and benzene. Then the crude product obtained was purified by recrystallization of column and chromatography or other suitable purification method.

Results are summarized in Table 3.

EXAMPLES 32 - 47

General Procedure

A mixture consisting of a phenoxyaliphatic acid derivative, an alcohol, a few drops of concentrated sulfuric acid and, if necessary, benzene was refluxed for a determined period of time, while removing produced water together with a solvent. The solvent was added to the reaction mixture to keep a constant amount. After the reaction was over, the mixture was washed with water, dried over anhydrous sodium sulfate and concentrated to yield a crude product, which was purified by recrystallization or column chromatography.

the results are summarized in Table 4.

TABLE 3

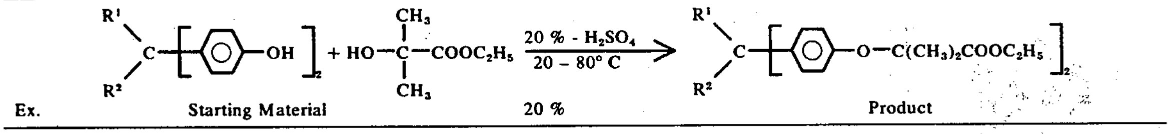

Ex. Starting Material 20 % Product

| Ex. | 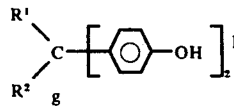 g | 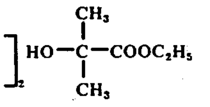 g | $H_2SO_4$ g | Reaction time (hrs.) | Chemical Structure (Yield g.) | Physical Property | Elementary analysis Cal. (%) | Found (%) |
|---|---|---|---|---|---|---|---|---|
| 30 | 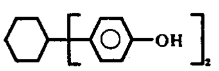 26.8 g | 26.4 g | 10 g | 1 50° C | 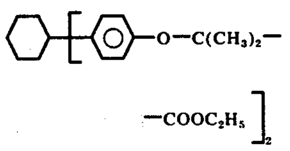 15 g | m.p. 103° - 104.5° C | C: 72.55 H: 8.12 | 72.31 8.07 |
| 31 | 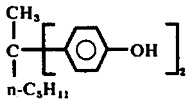 | 27 g | 20 g | 1.5 70° C | 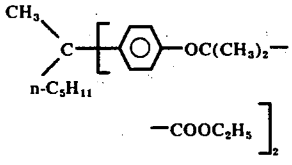 13 g | $n_D^{21}$ 1.5138 pale yellow oil | C: 72.62 H: 8.65 | 72.47 8.61 |

TABLE 4

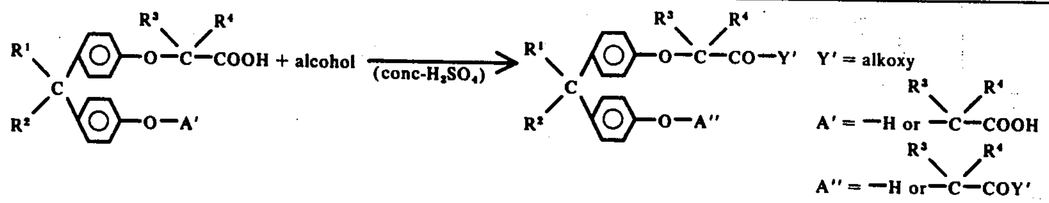

| Ex. No. | Starting Material 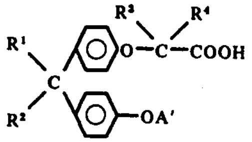 g | Alcohol g | Benzene g | Reaction Time (hrs.) | Product Chemical Structure | Physical Property | Elementary Analysis Cal. (%) | Elementary Analysis Found (%) |
|---|---|---|---|---|---|---|---|---|
| 32 | 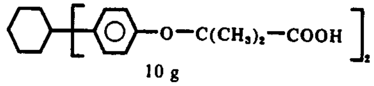 10 g | 99 % $C_2H_5OH$ 7.0 g | benzene 30 g | 10 | 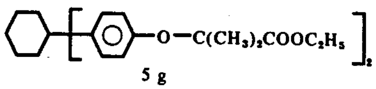 5 g | m.p. 103° - 104° C | C: 72.55, H: 8.12, | 72.12 8.10 |
| 33 | 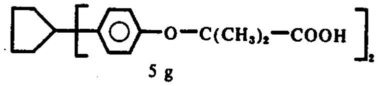 5 g | 99 % $C_2H_5OH$ 10 g | benzene 25 (ml) | 8 | 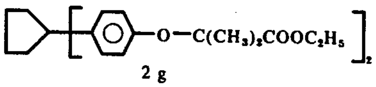 2 g | m.p. 73° - 75° C | C: 72.17, H: 7.94, | 72.49 7.92 |
| 34 | 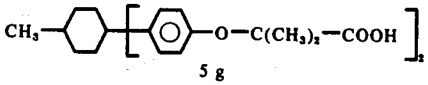 5 g | 99 % - $C_2H_5OH$ 30 g | benzene 20 g | 8 | 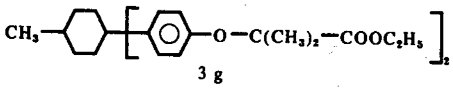 3 g | pale yellow oil $n_D^{23}$ 1.5280 | C: 72.91, H: 8.29, | 72.85 8.19 |
| 35 | 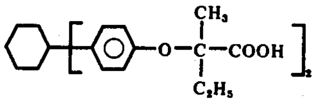 5 g | 99 % - $C_2H_5OH$ 20 g | benzene 20 g | 15 | 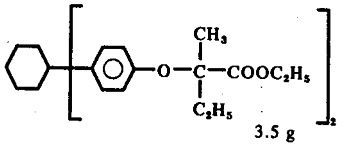 3.5 g | pale yellow oil $n_D^{23}$ 1.5295 | C: 73.25, H: 8.45, | 73.17 8.51 |
| 36 | 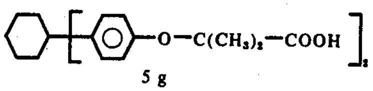 5 g | 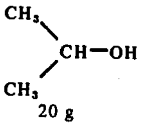 20 g | benzene 30 g | 30 | 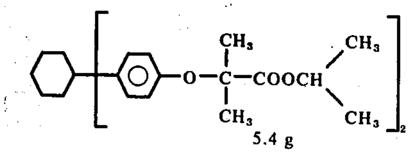 5.4 g | pale yellow oil $n_D^{24.5}$ 1.5193 | C: 73.25, H: 8.45, | 73.08 8.41 |

TABLE 4-continued

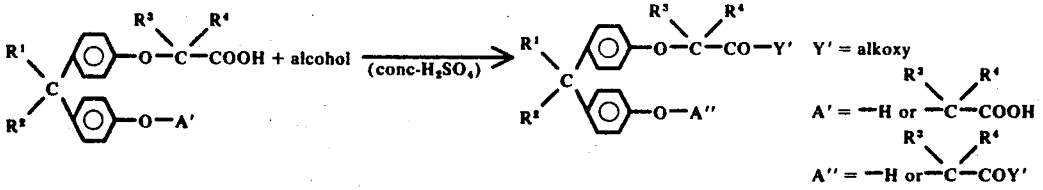

| Ex. No. | Starting Material 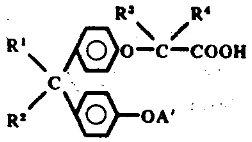 g | Alcohol g | Benzene g | Reaction Time (hrs.) | Product Chemical Structure | Physical Property | Elementary Analysis Cal. (%) | Elementary Analysis Found (%) |
|---|---|---|---|---|---|---|---|---|
| 37 | 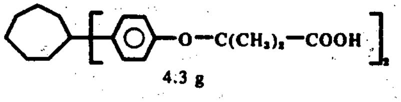 4.3 g | 99 % - $C_2H_5OH$ 15.0 g | benzene 20.0 g | 7 | 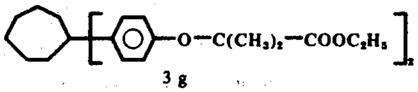 3 g | pale yellow oil $n_D^{23.5}$ 1.5274 | C: 72.91<br>H: 8.29 | 73.25<br>8.19 |
| 38 | 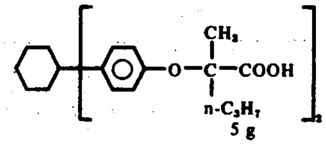 5 g | 99 % - $C_2H_5OH$ 20 g | benzene 20 g | 30 | 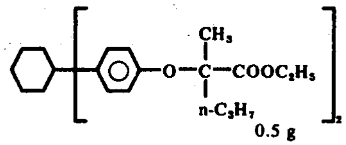 0.5 g | $n_D^{27.5}$ 1.5170 | C: 73.88<br>H: 8.75 | 73.63<br>8.74 |
| 39 | 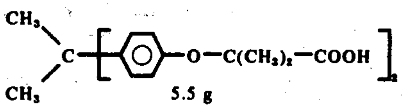 5.5 g | 99 % - $C_2H_5OH$ 20 g | benzene 20 g | 8 | 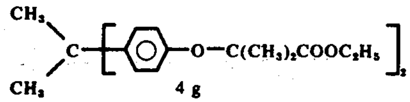 4 g | $n_D^{20.2}$ 1.5232 pale yellow oil | C: 71.02<br>H: 7.95 | 71.33<br>7.96 |
| 40 | 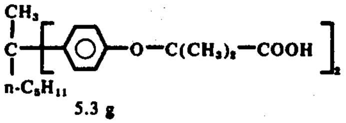 5.3 g | 99 % - $C_2H_5OH$ 10 g | benzene 20 g | 10 | 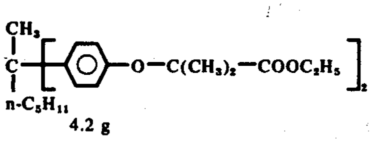 4.2 g | $n_D^{22}$ 1.5138 pale yellow oil | C: 72.62<br>H: 8.65 | 72.38<br>8.52 |
| 41 | 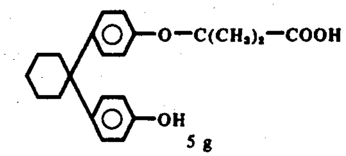 5 g | 99 % - $C_2H_5OH$ 100 ml | — | 8 | 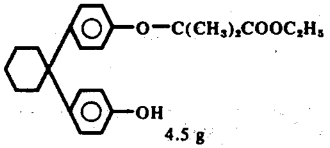 4.5 g | m.p. 117° - 118° C | C: 75.36<br>H: 7.91 | 75.55<br>8.06 |

TABLE 4-continued
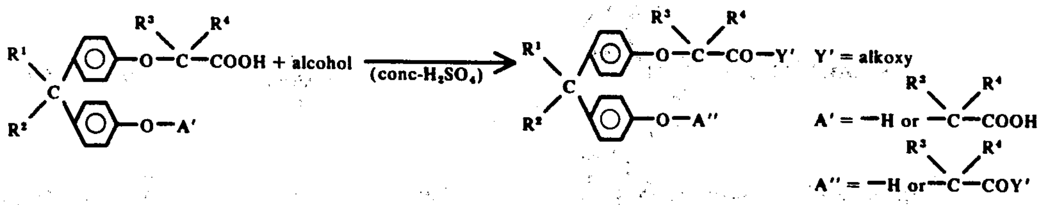
| Ex. No. | Starting Material 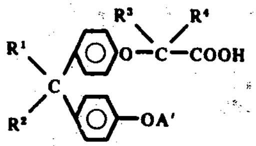 g | Alcohol g | Benzene g | Reaction Time (hrs.) | Product Chemical Structure | Physical Property | Elementary Analysis Cal. (%) | Found (%) |
|---|---|---|---|---|---|---|---|---|
| 42 | 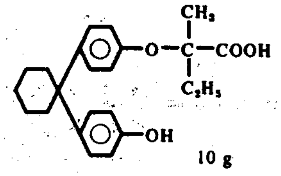 10 g | 99 % $C_2H_5OH$ 100 g | — | 8 | 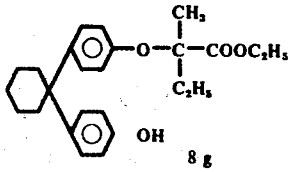 8 g | $n_D^{20.5}$ 1.5600 | C: 75.72,<br>H: 8.13, | 75.52<br>8.21 |
| 43 | 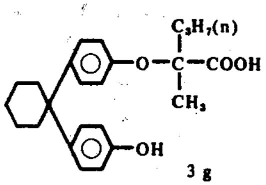 3 g | 99 % $C_2H_5OH$ 50 g | benzene 30 g | 18 | 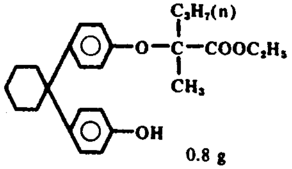 0.8 g | $n_D^{23.5}$ 1.5580 | C: 76.06,<br>H: 8.34, | 76.12<br>8.21 |
| 44 | 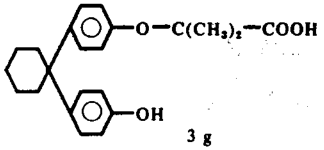 3 g | 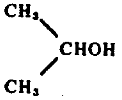 60 ml | — | 30 | 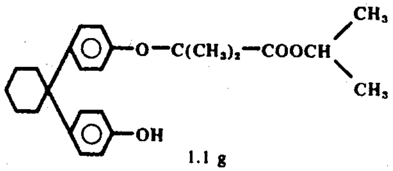 1.1 g | m.p. 108° – 110° C | C: 75.72,<br>H: 8.13, | 75.90<br>8.32 |

TABLE 4-continued
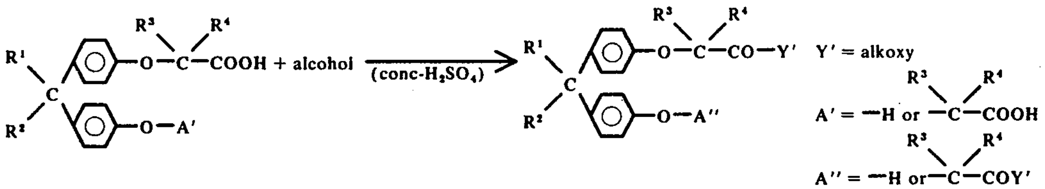
| Ex. No. | Starting Material 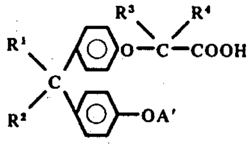 g | Alcohol g | Benzene g | Reaction Time (hrs.) | Product Chemical Structure | Physical Property | Elementary Analysis Cal. (%) | Elementary Analysis Found (%) |
|---|---|---|---|---|---|---|---|---|
| 45 | 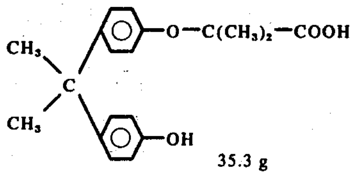 35.3 g | 99.5 % $C_2H_5OH$ 50 g | benzene 100 g | 10 | 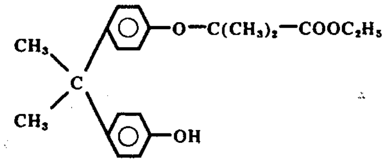 | $n_D^{22}$ 1.5472 | C: 73.66<br>H: 7.66 | 73.45<br>7.80 |
| 46 | 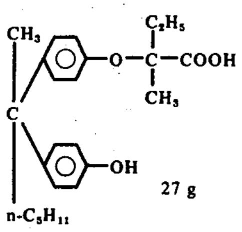 27 g | 99.5 % $C_2H_5OH$ 200 ml | benzene 100 g | 21.5 | 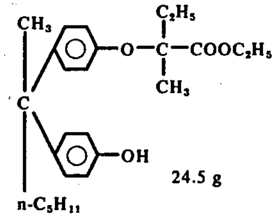 24.5 g | $n_D^{22}$ 1.5436 | C: 75.69<br>H: 8.80 | 75.90<br>8.69 |
| 47 | 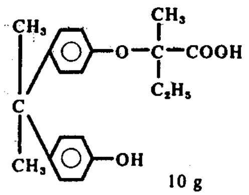 10 g | 99.5 % $C_2H_5OH$ 50 ml | benzene 50 ml | 21.5 | 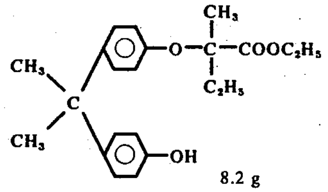 8.2 g | $n_D^{26.5}$ 1.5480 | C: 74.13<br>H: 7.92 | 74.40<br>7.98 |

EXAMPLES 48 - 51

General Procedure

An acid chloride was obtained by reacting a 1,1-bis-(4'-hydroxyphenyl) aliphatic acid derivative with thionyl chloride.

Into a mixture of an amine, dry ether and triethyl amine was added dropwise a mixture of the abovementioned acid chloride and dry ether, while keeping a temperature of 10°-15° C. After the addition, the reaction mixture was stirred at the same temperature and then refluxed for a few hours. After cooling crystals were collected by filtration and recrystallization from a suitable solvent.

The results are summarized in Table 5.

TABLE 5

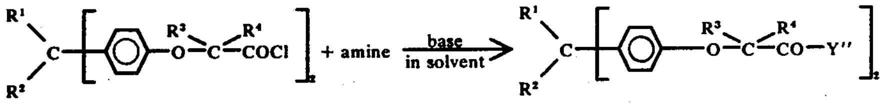

Y'' = amine residue

| Ex. | Starting Materials 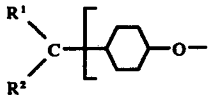 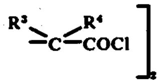 | amine | base | solvent | Reaction temp (° C) hours | Product Structure yield g | Physical Property | Elementary analysis Cal. (%) | Found (%) |
|---|---|---|---|---|---|---|---|---|---|
| 48 | 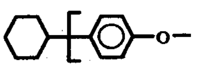<br>$-C(CH_3)_2-COCl]_2$<br>9 g | 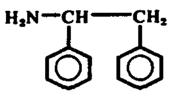<br>6.7 g | $N(C_2H_5)_3$<br>1.7 g | ether<br>50 ml +<br>50 ml | 20 - 30° C:<br>5 hrs.<br>reflux<br>2 hrs. | 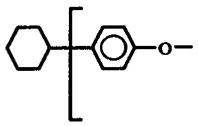<br>$-C(CH_3)_2-CONH-$<br>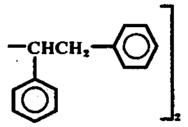<br>3 g | m.p.<br>148.5 - 150° C | C: 81.17,<br>H: 7.31,<br>N: 3.50, | 80.95<br>7.12<br>3.67 |
| 49 | 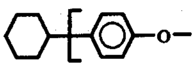<br>$-C(CH_3)_2-COCl]_2$<br>5 g | 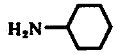<br>2.1 g | $N(C_2H_5)_3$<br>2.1 g | ether<br>30 ml | 10° C:<br>1 hr.<br>20 - 30° C:<br>3 hrs.<br>reflux:<br>2 hrs. | 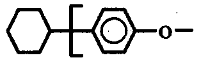<br>$-C(CH_3)_2-$<br>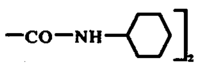 | m.p.<br>109 - 110° C | C: 75.71,<br>H: 9.03,<br>N: 4.65, | 75.42<br>9.33<br>4.86 |
| 50 | 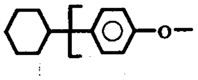<br>$-C(CH_3)_2COCl]_2$<br>5 g | 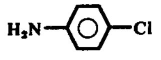<br>2.7 g | $N(C_2H_5)_3$<br>2.2 g | ether<br>15 ml<br>+ 20<br>ml | 10° C:<br>2 hrs.<br>20 - 30° C:<br>3 hrs.<br>reflux:<br>2 hrs. | 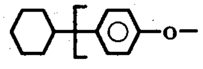<br>$-C(CH_3)_2-CONH-$<br>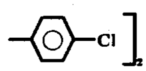 | m.p.<br>135° - 137° C | C: 69.20,<br>H: 6.07,<br>N: 4.25,<br>Cl: 10.77, | 69.08<br>6.23<br>4.45<br>10.75 |

TABLE 5-continued

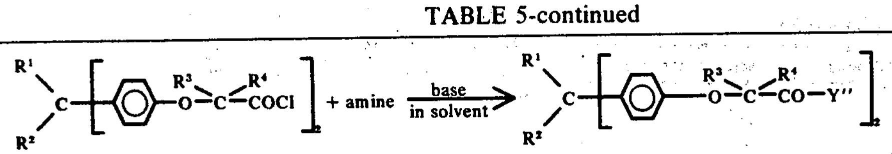

Y'' = amine residue

| Ex. | Starting Materials 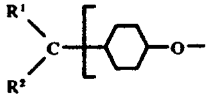 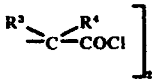 | amine | base | solvent | Reaction temp (° C) hours | Product Structure yield g. | Physical Property | Elementary analysis Cal. (%) | Found (%) |
|---|---|---|---|---|---|---|---|---|---|
| 51 | 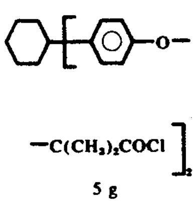 5 g | 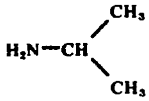 1.24 g | $N(C_2H_5)_3$ 2.12 g | ether 30 ml | 10° C: 1 hr. 20 - 30° C: 2 hrs. reflux: 2 hrs. | 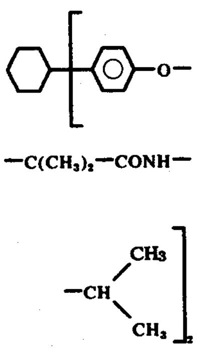 | m.p. 133° - 134° C | C: 73.53, H: 8.87, N: 5.36, | 73.36 8.91 5.52 |

EXAMPLE 52

Preparation of cyclo-$C_6H_{10}$-[p-$C_6H_4OC(CH_3)_2CONH_2]_2$

Into a mixture of 28% aqueous ammonia (10 ml.) and 1,2-dichloroethane (50 ml.) was added dropwise a mixture of 1,2-dichloroethane (30 ml.) and an acid chloride (9 g) which was obtained by reacting 10 g of 1,1-bis(4'-hydroxyphenyl) cyclohexane-0,0-diisobutyric acid and 5 g of thionyl chloride. The temperature of the reaction mixture was kept at 0°–5° C during the addition. After the completion of the addition, the reaction mixture was stirred at 10° C for 5 hours, washed with water and dried. The solvent was distilled off to give a pale yellow crystal (4 g) of the desired product, which was purified by recrystallization.

| Elementary analysis | C (%) | H (%) | N (%) |
|---|---|---|---|
| Cal. | 71.20 | 7.82 | 6.39 |
| Found | 70.92 | 7.76 | 6.37 |

EXAMPLE 54

Preparation of $(CH_3)_2C$-[p-$C_6H_4$-o-$(CH_3)_2COOK]_2$

The dicarboxylic acid obtained in Example 5 was treated with 10%-KOH aqueous solution with gentle heating to yield colorless plates which was slightly soluble in water. m.p. > 220° C.

The cholesterol lowering activity of above prepared compounds was tested in mice injected with 500 mg/kg, i.v. of Triton WR 1339*. (trademark for oxyethylated tert.-octylphenol formaldehyde polymer, manufactured by Rohm & Haas Co., U.S.A.) The test compounds were orally administered in a dose of 50 mg/kg immediately after the injection of Triton solution and 24 hours after the injection, mice were sacrificed for analysis of serum cholesterol. Cholesterol lowering effect was expressed as percentage of serum cholesterol levels of control group as a shown in the following Table 6. In the Table 6, compounds are referred to by number of the above-mentioned Examples.

Table 6

| Compounds (No.) | Cholesteral lowering effect (%) |
|---|---|
| 2 | −19 |
| 4 | −64 |
| 6 | −29 |
| 7 | −55 |
| 8 | −24 |
| 10 | −19 |
| 11 | −20 |
| 12 | −19 |
| 14 | −57 |
| 15 | −83 |
| 16 | −89 |
| 17 | −58 |
| 18 | −18 |
| 19 | −25 |
| 20 | −70 |
| 21 | −50 |
| 22 | −20 |
| 23 | −43 |
| 24 | −20 |
| 25 | −38 |
| 26 | −22 |
| 27 | −34 |
| 28 | −42 |
| 29 | −60 |
| 31 | −20 |
| 33 | −20 |
| 34 | −21 |
| 36 | −22 |
| 42 | −64 |
| 43 | −27 |
| 44 | −47 |

Table 6-continued

| Compounds (No.) | Cholesteral lowering effect (%) |
|---|---|
| 46 | −18 |
| 47 | −56 |
| 48 | −20 |
| 49 | −21 |
| 50 | −25 |
| 51 | −19 |
| 52 | −20 |
| 53 | −32 |
| 54 | −42 |
| Clofibrate | −16 |

What we claim is:

1. A phenoxyaliphatic carboxylic acid derivative of the formula,

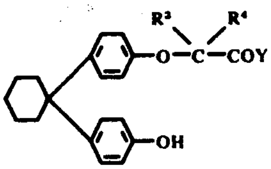

wherein $R^3$ is methyl, $R^4$ is methyl, ethyl, or n-propyl and Y is hydroxyl or $C_1$-$C_4$ alkoxy.

2. Phenoxyaliphatic carboxylic acid derivative of the formula,

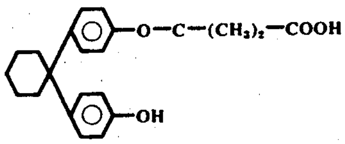

3. Phenoxyaliphatic carboxylic acid derivative of the formula,

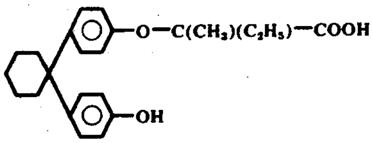

* * * * *